US006756203B2

(12) United States Patent
Kieff et al.

(10) Patent No.: US 6,756,203 B2
(45) Date of Patent: Jun. 29, 2004

(54) ASSAYS FOR COMPOUNDS THAT MODULATE RHADINO VIRUS LANA ACTION IN TRANS ON A UNIT OF RHADINO VIRUS DNA TO MEDIATE EFFICIENT EPISOME PERSISTENCE

(75) Inventors: Elliott D. Kieff, 269 Lee St., Brookline, MA (US) 02445; Mary E. Ballestas, Beverly, MA (US); Kenneth M. Kaye, Weston, MA (US)

(73) Assignee: Elliott D. Kieff, Brookline, MA (US)

( * ) Notice: Subject to any disclaimer, the term of this patent is extended or adjusted under 35 U.S.C. 154(b) by 90 days.

(21) Appl. No.: 09/894,273

(22) Filed: Jun. 28, 2001

(65) Prior Publication Data

US 2004/0037847 A1 Feb. 26, 2004

Related U.S. Application Data

(62) Division of application No. 09/298,568, filed on Apr. 21, 1999, now Pat. No. 6,322,792.
(60) Provisional application No. 60/109,422, filed on Nov. 19, 1998.

(51) Int. Cl.$^7$ .............................. C12Q 1/68; C12P 21/06
(52) U.S. Cl. ........................... 435/6; 435/69.1; 435/975; 536/23.72
(58) Field of Search ............................... 435/5, 69.1, 8, 435/6, 975; 935/24; 536/23.72

(56) References Cited

U.S. PATENT DOCUMENTS

| 4,581,847 A | 4/1986 | Hibberd et al. |
| 4,761,373 A | 8/1988 | Anderson et al. |
| 5,861,240 A | 1/1999 | Ganem et al. .................. 435/5 |

FOREIGN PATENT DOCUMENTS

| WO | WO8704181 | 6/1987 |
| WO | WO8804300 | 6/1988 |
| WO | WO8911789 | 12/1989 |

OTHER PUBLICATIONS

PCT Written Opinion, PCT/US99/27508.
PCT Search Report, PCT/US99/27508.
Kedes et al. "Identification of the Gene Encoding the Major Latency–associated Nuclear Antigen of the Kaposi's Sarcoma–associated Herpesvirus." Journal of Clinical Investigation, Nov. 1997, vol. 100, No. 10, pp. 2606–2610.
Sun et al. "A viral gene that activates lytic cycle expression of Kaposi's sarcoma–associated hypersvirus." Proc. Natl. Acad. Sci. USA, Sep. 1998, vol. 95, pp. 10866–10871.
Ballestas et al. "Efficient Persistence of Extrachromosomal KSHV DNA Mediated by Latency–Associated Nuclear Antigen." Science, Apr. 23, 1999, vol. 284, pp. 641–644.
Y. Chang, et al., Science, vol. 266, pp. 1865–1869 (1994).
P.S. Moore, et al., J. Virol., vol. 70, p. 549 (1996).

S.J. Gao, et al., N. Engl. J. Med., vol. 335, pp. 233–241 (1996).
P.S. Moore, et al. N. Engl. J. Med., vol. 332, p. 1181 (1995).
E. Cesarman, et al., Blood, vol. 86, p. 2708 (1995).
M.B. Rettig, et al., Science, vol. 276, p. 1851 (1997).
J. Soulier, et al., Blood, vol. 86, pp. 1276–1280 (1995).
E. Cesarman, et al., N. Engl. J. Med., vol. 332, pp. 1186–1191 (1995).
L.L. Decker, et al., J. Exp. Med., vol. 184, pp. 283–288 (1996).
J. Yates, et al., Proc. Natl. Acad. Sci. USA, vol. 81, pp. 3806–3810 (1984).
J.L. Yates, et al., Nature, vol. 313, p. 812 (1985).
D.R. Rawlins, et al., Cell, vol. 42, p. 859 (1985).
S.H. Kung, et al., J. Virol., vol. 70, p. 1738 (1996).
J.J. Russo, et al., Proc. Natl. Acad. Sci. USA, vol. 93, pp. 14862–14867 (1996).
P. Kellam, et al., J. of Human Virol., vol. 1, pp. 19–29 (1997).
L. Rainbow, et al., J. Virol., vol. 71, pp. 5915–5921 (1997).
D.H. Kedes, et al., J. Clin. Invest., vol. 100, pp. 2606–2610 (1997).

(List continued on next page.)

Primary Examiner—Ali R. Salimi
(74) Attorney, Agent, or Firm—F. Scott Kieff

(57) ABSTRACT

Primary effusion lymphoma (PEL) cells harbor Kaposi's sarcoma-associated herpesvirus (KSHV) episomes and express a KSHV encoded latency-associated nuclear antigen (LANA). In PEL cells, LANA and KSHV DNA co-localized in dots in interphase nuclei and along mitotic chromosomes. In the absence of KSHV DNA, LANA was diffusely distributed in the nucleus or on mitotic chromosomes. In lymphoblasts, LANA was necessary and sufficient for the persistence of episomes containing a specific KSHV DNA fragment. Furthermore, LANA co-localized with the artificial KSHV DNA episomes in nuclei and along mitotic chromosomes. The KSHV DNA segment that provides for efficient persistence in LANA positive cells has been identified as the rhodino virus cis-acting element (RVCAE). These results support a model in which LANA tethers episomes containing the KSHV RVCAE DNA to chromosomes during mitosis to enable efficient segregation to progeny cells. The products and methods of the invention are useful in identifying compounds for modulating (especially including interfering with) the persistence of rhodino virus DNA in mammalian cells, and disease states associated therewith, as well as such compounds themselves. The products and methods of the invention are also useful in modulating (especially including enabling or improving) the efficient persistence of a heterologous DNA containing RVCAE and a selected DNA in mammalian cells in which LANA is expressed for use in gene therapies and related techniques based on the selected DNA.

6 Claims, 8 Drawing Sheets

OTHER PUBLICATIONS

Figure 1:
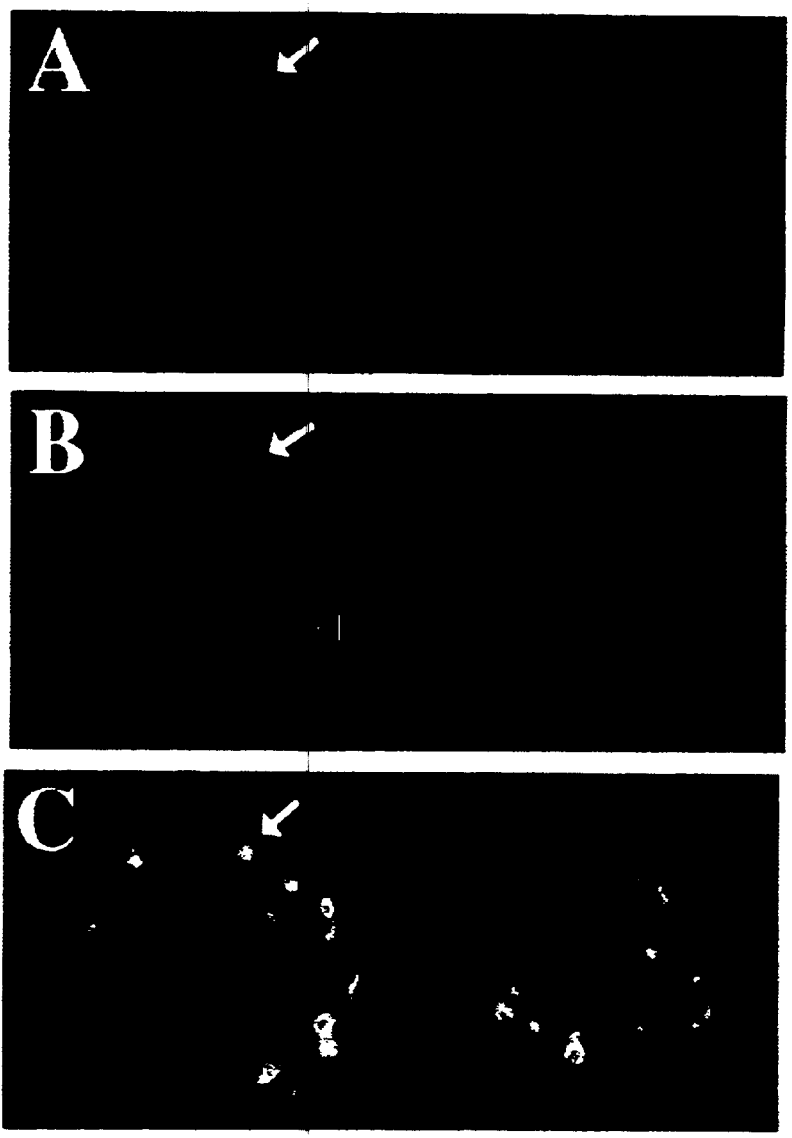

F. Neipel, et al., *J. Virol.*, vol. 71, pp. 4187–4192 (1997).
J.C. Albrecht, et al., *J. Virol.*, vol. 66, pp. 5047–5058 (1992).
H.W. Virgin IV, et al., *J. Virol.*, vol. 71, pp. 5894–5904 (1997).
S.J. Gao, et al., *Nature Medicine*, vol. 2, pp. 918, 925–8 (1996).
D. Jones, et al., *N. Engl. J. of Med.*, vol. 339, pp. 444–449 (1998).
R. Renne, et al., *Nature Medicine*, vol. 2, pp. 342–346 (1996).
L. Szekely, et al., *J. of General Virology*, vol. 79, p. 1445 (1998).
T. Gardella, et al., *J. of Virol*, vol. 50, pp. 248–254 (1984).
R. Reene, et al., *J. Virol.*, vol. 70, p. 8151 (1996).
Lagunoff, et al., *Virology*, p. 236 (1997).
Ehtisham, et al., *J. Virol.*, vol. 67, pp. 5247–5252 (1993).
Sunil–Chandra, et al., *Am. J. Pathol.*, vol. 145, pp. 818–826 (1994).
Melendez, et al., *Lab. Anim. Care*, vol. 18, pp. 374–381 (1968).
Daniel, et al., *J. Natl. Cancer Inst.*, vol. 53, pp. 1803–1807 (1974).
Melendez, et al., *Lab Anim. Care*, vol. 19, pp. 378–386 (1969).
Biesinger, et al., *Proc. Natl. Acad Sci. USA*, vol. 89, pp. 3116–3119 (1992).
Medveczky, et al., *Virology*, vol. 196, pp. 402–412 (1993).
Martin, et al., *N. Engl. J. Med.*, vol. 338, pp. 948–954 (1998).
Angeloni, et al., *J. Infect. Dis.*, vol. 177, pp. 1715–1718 (1998).
Blauvelt, et al., *J. Infect. Dis.*, vol. 176, pp. 771–774 (1997).
Chandren, et al., *Virology*, vol. 243, pp. 208–217 (1998).
Kedes, et al., *Jama*, vol. 277, 478–81 (1997).
Kedes, et al., *Nat. Med.*, vol. 2, 918–24 (1996).
Lennette, et al., *Lancet*, vol. 348, pp. 858–861 (1996).
Simpson, et al., *Lancet*, vol. 348, pp. 1133–1138 (1996).
Chang, et al., *Arch. Intern. Med.*, vol. 156, pp. 202–204 (1996).
Foreman, et al., *J. Clin. Invest.*, vol. 99, pp. 2971–2978 (1997).
Miller, et al., *N. Engl. J. Med.*, vol. 334, pp. 1292–1297 (1996).
Moore, et al., *Aids*, vol. 10, pp. 175–180 (1996).
Said, et al., *Blood*, vol. 88, pp. 3124–3128 (1996).
Kikuta, et al., *Br. J. Haematol*, vol. 99, pp. 790–793 (1997).
Miller, et al., *J. Virol.*, vol. 71, pp. 314–324 (1997).
Staskus, et al., *J. Virol.*, vol. 71, pp. 715–719 (1997).
Sturzl, et al., *Int. J. Cancer*, vol. 72, pp. 68–71 (1997).
Zhong, et al., *Proc. Natl. Acad. Sci. USA*, vol. 93, pp. 6641–6646 (1996).
Gahn, et al., *J. Virol.*, vol. 69, 2633–6 (1995).
Lupton, et al., *Molecular and Cellular Biology*, vol. 5, pp. 2533–2542 (1985).
Platt, et al., *J. Virol.*, vol. 67, pp. 1739–1745 (1993).
Moore et al., *Science*, vol. 274, pp. 1739–1744 (1996).
Sarid et al., *J. Virol*, vol. 72, pp. 1005–1112 (1998).
Muralidhar et al., *J. Virol.*, vol. 72, pp. 4980–4988 (1998).
Cesarman et al., *J. Virol.*, pp. 8218–8223 (1996).
D. Reisman, B. Sugden, *Molecular and Cellular Biology*, vol. 6, p. 3838 (1986).
J. Wiezorek, et al., First Annual Meeting on Kaposi's sarcoma–associated herpes virus and related Agents, Univ. of CA, Santa Cruz, Jul. 25–28 (1998).
D. Reisman, B. Sugden, *Molecular and Cellular Biology*, vol. 6, p. 3838 (1986).
Ausubel, et al., eds., 1989, *Current Protocols in Molecular Biology*, vol. I, Green Publishing Associates, Inc., and John Wiley & Sons, Inc., New York, at p. 2–10.3.
Sambrook, J., et al., (1989) *Molecular Cloning*, Colo. Spring Harbor Press, USA, pp. 9.47–9.55.
Southern et al., *J. Mol. Appl. Gen.*, vol. I, pp. 327–341 (1982).
Shimizu et al., *Mol. Cell Biol.*, vol. 6, pp. 1074–1087 (1986).
Kwok et al., *Proc. Nat'l. Acad. Sci. USA*, pp. 4552–4555 (1986).
Deblock et al., *Embo J.*, vol. 6, pp. 2513–2518 (1987).
Buchanan–Wollaston et al., *J. Cell. Biochem.*, Supp. 13D, p. 330 (1989).
G.W. Haughn et al., *Mol. Gen. Genet.*, vol. 211, pp. 266–271 (1988).
Comai et al., *Nature*, vol. 317, pp. 741–744 (1985).
Parker et al., *Plant Physiol.*, vol. 92, p. 1220 (1990).
Guerineau et al., *Plant Molec. Biol.*, vol. 15, pp. 127–136 (1990).
Hirschberg et al., *Science*, vol. 222, pp. 1346–1349 (1983).
A. Bochkarev, et al., *Cell*, vol. 84, p. 791 (1996).
Harada, et al., *J. Virology*, vol. 72, pp. 9948–9958 (1998).
Kaelin, W.G., et al., *Cell*, vol. 70, pp. 351–364 (1992).
Izant et al., *Cell*, vol. 36, pp. 1007–1015 (1984).
Rosenberg et al., *Nature*, vol. 313, pp. 703–706 (1985).
Haseloff, et al., *Nature*, vol. 334, pp. 585–591 (1988).
Zaug, et al., *Science*, vol. 224, pp. 574–578 (1984).
Zaug and Cech, *Science*, vol. 231, pp. 470–475 (1986).
Zaug, et al., *Nature*, vol. 324, pp. 429–433 (1986).
Been et al., *Cell*, vol. 47, pp. 207–216 (1986).
Llewellyn et al., *J. Mol. Biol.*, vol. 195, pp. 115–123 (1987).
L. Petti, et al., *Virology*, vol. 176, p. 563 (1990).
E. Grogan, et al., *Proc. Natl. Acad. Sci. USA*, vol. 80, p. 7650 (1983).
B.M. Reedman, et al., *Int. J. Cancer*, vol. 11, p. 499 (1973).
E. Hatzivassiliou, et al., *Biochemistry*, vol. 36, p. 9221 (1997).
K.M. Kaye, et al., *J. of Virol.*, vol. 69, p. 675 (1995).
D. Liebowitz, et al., *J. of Virol.*, vol. 66, p. 4612 (1992).

FIG. 6

```
ATGGCGCCCCCGGGAATGCGCCTGAGGTCGGGACGGAGCACCGGCGCGCCCTTAACGAGAGGAAGTTGTAGGAAA
CGAAACAGGTCTCCGGAAAGATGTGACCTTGGCGATGACCTACATCTACAACCGCGAAGGAAGCATGTCGCCGAC
TCCATCGACGGCCGGGAATGTGGACCCCACACCTTGCCTATACCTGGAAGTCCCACAGTGTTCACATCCGGGCTG
CCAGCATTTGTGTCTAGTCCTACTTTACCGGTGGCTCCCATTCCTTCACCCGCTCCCGCAACACCTTTACCTCCA
CCGGCACTCTTACCCCCCGTAACCACGTCTTCCTCCCCAATCCCTCCATCCCATCCTGTGTCTCCGGGGACCACG
GATACTCATTCTCCATCTCCTGCATTGCCACCCACGCAGTCTCCAGAGTCTTCTCAAAGGCCACCGCTTTCAAGT
CCTACAGGAAGGCCAGACTCTTCAACACCTATGCGTCCGCCACCCTCGCAGCAGACTACACCTCCACACTCACCC
ACGACTCCTCCACCCGAGCCTCCCTCCAAGTCGTCACCAGACTCTTTAGCTCCGTCTACCCTGCGTAGCCTGAGA
AAAAGAAGGCTATCGTCCCCCCAAGGTCCCTCTACACTAAACCCAATATGTCAGTCGCCCCCAGTCTCTCCCCCT
AGATGTGACTTCGCCAACCGTAGTGTGTACCCCCCATGGGCCACAGAGTCCCCGATCTACGTGGGATCATCCAGC
GATGGCGATACTCCGCCACGCCAACCGCCTACATCTCCCATCTCCATAGGATCATCATCCCCGTCTGAGGGATCC
TGGGGTGATGACACAGCCATGTTGGTGCTCCTTGCGGAGATTGCAGAAGAAGCATCCAAGAATGAAAAAGAATGT
TCCGAAAATAATCAGGCTGGCGAGGATAATGGGGACAACGAGATTAGCAAGGAAAGTCAGGTTGACAAGGATGAC
AATGACAATAAGGATGATGAGGAGGAGCAGGAGACAGATGAGGAGGACGAGGAGGATGACGAGGAGGATGACGAG
GAGGATGACGAGGAGGATGACGAGGAGGATGACGAGGAGGATGACGAGGAGGATGACGAGGAGGATGACGAGGAG
GATGACGAGGAGGATGACGAGGAGGATGACGAGGAGGAGGACGAGGAGGAGGACGAGGAGGAGGACGAGGAGGAG
GAGGACGAGGAGGATGACGATGATGAGGACAATGAGGACGAGGAGGATGACGAGGAGGAGGACAAGAAGGAGGAC
GAGGAGGACGGGGGCGATGGAAACAAAACGTTGAGCATCCAAAGTTCACAACAGCAGCAGGAGCCACAACAGCAG
GAGCCACAGCAGCAGGAGCCACAGCAGCAGGAGCCCCTGCAGGAGCCACAACAGCAGGAGCCACAGCAGCAGGAG
CCACAGCAGCAGGAGCCCCTGCAGGAGCCACAACAGCAGGAGCCACAGCAGCAGGAGCCCCTGCAGGAGCCACAA
CAGCAGGAGCCACAACAGCAGGAGCCACAGCAGCAGGAGCCACAGCAGCAGGAGCCACAGCAGCAGGAGCCACAG
CAGCAGGAGCCACAGCAGCAGGAGCCACAGCAGCAGGAGCCACAGCAGCAGGAGCCACAGCAGCAGGAGCCACAG
CAGCGGGAGCCACAGCAGCGGGAGCCCCAGCAGCGGGAGCCACAGCAGCGGGAGCCACAGCAGCGGGAGCCACAG
CAGCGGGAGCCACAGCAGCGGGAGCCACAGCAGCGGGAGCCACAGCAGCGGGAGCCACAGCAGCAGGATGAGCAG
CAGCAGGATGAGCAGCAGCAGGATGAGCAGCAGCAGGATGAGCAGCAGCAGGATGAGCAGCAGCAGGATGAGCAG
CAGCAGGATGAGCAGCAGCAGGATGAGCAGCAGCAGGATGAGCAGCAGCAGGATGAGCAGCAGCAGGATGAGCAG
CAGCAGGATGAGCAGCAGCAGGATGAGCAGCAGCAGGATGAGCAGCAGCAGGATGAGCAGCAGCAGGATGAGCAG
CAGCAGGATGAGCAGCAGCAGGATGAGCAGCAGCAGGATGAGCAGCAGCAGGATGAGCAGCAGCAGGATGAGCAG
GAGCAGCAGGATGAGCAGGAGCAGCAGGATGAGCAGGAGCAGCAGGATGAGCAGCAGCAGGATGAGCAGCAGCAG
CAGGATGAGCAGCAGCAGGATGAGCAGCAGCAGGATGAGCAGCAGCAGCAGGATGAGCAGCAGCAGCAG
GATGAACAGGAGCAGCAGGAGGAGCAGGAGCAGCAGGAGGAGCAGGAGCAGGAGTTAGAGGAGCAGGAGCAGGAG
TTAGAGGATCAGGAGCAGGAGTTAGAGGAGCAGGAGCAGGAGTTAGAGGAGCAGGAGCAGGAGTTAGAGGAGCAG
GAGCAGGAGTTAGAGGAGCAGGAGCAGGAGTTAGAGGAGCAGGAGCAGGAGTTAGAGGAGCAGGAGCAGGAGTTA
GAGGAGCAGGAGCAGGAGTTAGAGGAGCAGGAGCAGGAGTTAGAGGAGCAGGAGGTGGAAGAGCAAGAGCAGGAG
GTGGAAGAGCAAGAGCAGGAGCAGGAAGAGCAGGAATTAGAGGAGGTGGAGGAGCAAGAGCAGGAGCAGGAGGAG
CAGGAGGAGCAGGAGTTAGAGGAGGTGGAAGAGCAGGAAGAGCAGGAGTTAGAGGAGGTGGAAGAGCAGGAAGAG
CAGGAGTTAGAGGAGGTGGAAGAGCAGGAGCAGCAGGAGTTAGAGGAGGTGGAAGAGCAGGAGCAGCAGGGGGTG
GAACAGCAGGAGCAGGAGACGGTGGAAGAGCCCATAATCTTGCACGGGTCGTCATCCGAGGACGAAATGGAAGTG
GATTACCCTGTTGTTAGCACACATGAACAAATTGCCAGTAGCCCACCAGGAGATAATACACCAGACGATGACCCA
CAACCTGGCCCATCTCGCGAATACCGCTATGTACTCAGAACATCACCACCCCACAGACCTGGAGTTCGTATGAGG
CGCGTTCCAGTTACCCACCCAAAAAAGCCACATCCAAGATACCAACAACCACCGGTCCCTTACAGACAGATAGAT
GATTGTCCTGCGAAAGCTAGGCCACAACACATCTTTTATAGACGCTTTTTGGGAAAGGATGGAAGACGAGATCCA
AAGTGTCAATGGAAGTTTGCAGTGATTTTTTGGGGCAATGACCCATACGGACTTAAAAAATTATCTCAGGCCTTC
CAGTTTGGAGGAGTAAAGGCAGGCCCCGTGTCCTGCTTGCCCCACCCTGGACCAGACCAGTCGCCCATAACTTAT
TGTGTATATGTGTATTGTCAGAACAAAGACACAAGTAAGAAAGTACAAATGGCCCGCCTAGCCTGGGAAGCTAGT
CACCCCCTGGCAGGAAACCTACAATCTTCCATAGTTAAGTTTAAAAAGCCCCTGCCATTAACCCAGCCAGGGGAA
AACCAAGGTCCTGGGGACTCTCCACAGGAAATGACATAA
```

FIG. 7

MAPPGMRLRSGRSTGAPLTRGSCRKRNRSPERCDLGDDLHLQPRRKHVADSIDGRECGPHTL
PIPGSPTVFTSGLPAFVSSPTLPVAPIPSPAPATPLPPPALLPPVTTSSSPIPPSHPVSPGT
TDTHSPSPALPPTQSPESSQRPPLSSPTGRPDSSTPMRPPPSQQTTPPHSPTTPPPEPPSKS
SPDSLAPSTLRSLRKRRLSSPQGPSTLNPICQSPPVSPPRCDFANRSVYPPWATESPIYVGS
SSDGDTPPRQPPTSPISIGSSSPSEGSWGDDTAMLVLLAEIAEEASKNEKECSENNQAGEDN
GDNEISKESQVDKDDNDNKDDEEEQETDEEDEEDDEEDDEEDDEEDDEEDDEEDDEEDDEED
DEEDDEEDDEEDDEEEDEEEDEEEDEEEDEEDDDDEDNEDEEDDEEEDKKEDEEDGGDGNK
TLSIQSSQQQQEPQQQEPQQQEPQQQEPLQEPQQQEPQQQEPQQQEPQQQEPLQEPQQQEPQQQEPL
QEPQQQEPQQQEPQQQEPQQQEPQQQEPQQQEPQQQEPQQQEPQQQEPQQQEPQQQEPQQREPQQRE
PQQREPQQREPQQREPQQREPQQREPQQREPQQREPQQQDEQQQDEQQQDEQQQDEQQQDEQ
QQDEQQQDEQQQDEQQQDEQQQDEQQQDEQQQDEQQQDEQQQDEQQQDEQQQDEQQQDEQQ
DEQQQDEQQQDEQQQDEQQDEQEQQDEQEQQDEQQQDEQQQQDEQQQQDEQQQQDEQQQQ
DEQQQQDEQEQQEEQEQQEEQEQELEEQEQELEDQEQELEEQEQELEEQEQELEEQEQELEE
QEQELEEQEQELEEQEQELEEQEQELEEQEQELEEQEVEEQEQEVEEQEQEEQELEEVEE
QEQEQEEQEEQELEEVEEQEEQELEEVEEQEEQELEEVEEQEQQELEEVEEQEQGVEQQEQ
ETVEEPIILHGSSSEDEMEVDYPVVSTHEQIASSPPGDNTPDDDPQPGPSREYRYVLRTSPP
HRPGVRMRRVPVTHPKKPHPRYQQPPVPYRQIDDCPAKARPQHIFYRRFLGKDGRRDPKCQW
KFAVIFWGNDPYGLKKLSQAFQFGGVKAGPVSCLPHPGPDQSPITYCVYVYCQNKDTSKKVQ
MARLAWEASHPLAGNLQSSIVKFKKPLPLTQPGENQGPGDSPQEMT

FIG. 8

CGTGAACACCCCGCGCCCCGCGCCCCCACACCGCGCCGCCCCTCCCCCTCCCCCCGCTCGC
CTCCCGGCGCTGCCGCCAGGCCCCGGCCGGAGCCGGCCGCCCGCGGGGGGCAGGGCGCGCCC
GGCGGCTCCCTCGCGGGGCGGGGGACGGGGGAGGGGGGCGCCGGGCCCCCGCGCGCCGCGGC
AGCGGAGCGCGAGCGCCCCGCCGGCCGCCAGCGGCGGCGCAGGCCCCGGGGCCCCGAGCCC
CGAGCCCCGCCGGGGTACGGGGCTAGGCCACGCCTACTTTTTTTTCGGGCGGCCCCCCGAC
CCTCTCTCGGCCCCCGGTCCCCGCGGCCCGCGCGCGCCCCCCGGGGGGGTAAAACAGGGG
GGGGGGGATGCGGCCGCGGCGGCGCCCGCGGCGGCGGCGGCGCTTGCTTTCGTTTTCTCCCG
CGGCCCCCGGGCGCGAGCCGCGCGGCGGCGGCGGGCGCCCCCTCCCCCGGGGGGCTCGGCG
GGGGGCCCCCTGTCCCCGCGCGGGCCCGCGACCCCCGGCGCCGCCGCGCCCCGATCCCGCGG
GCGCCCCGCCCCCTGCCGGGGACGCCGCCGGGCCTGCGGCGCCTCCCGCCCGGGCATGGGG
CCGCGCGCCGCCTCAGGGCCCGGCGCGGCCGGCGCCTGGTCCCCGCCCCCGCCCGCGGGGA
CCCCGGGCAGCGAGGGAAGGGGGCGCCCTCTCTCTACTGTGCGAGGAGTCTGGGCTGCTGTG
TGTGAGCCTGTTTGGGGGAGCCTCCTCAGTGCTTGCTACGTGGAGCCCTGGACACTA

SEQUENCE LISTING

<160> NUMBER OF SEQ ID NOS: 3

<210> SEQ ID NO 1
<211> LENGTH: 3489
<212> TYPE: DNA
<213> ORGANISM: Kaposi's sarcoma-associated herpesvirus

<400> SEQUENCE: 1

```
atggcgcccc cgggaatgcg cctgaggtcg ggacggagca ccggcgcgcc cttaacgaga      60
ggaagttgta ggaaacgaaa caggtctccg gaaagatgtg accttggcga tgacctacat     120
ctacaaccgc gaaggaagca tgtcgccgac tccatcgacg gccgggaatg tggaccccac     180
accttgccta tacctggaag tcccacagtg ttcacatccg ggctgccagc atttgtgtct     240
agtcctactt taccggtggc tcccattcct tcacccgctc ccgcaacacc tttacctcca     300
ccggcactct tacccccgt aaccacgtct tcctccccaa tccctccatc ccatcctgtg     360
tctccgggga ccacggatac tcattctcca tctcctgcat tgccacccac gcagtctcca     420
gagtcttctc aaaggccacc gctttcaagt cctacaggaa ggccagactc ttcaacacct     480
atgcgtccgc caccctcgca gcagactaca cctccacact cacccacgac tcctccaccc     540
gagcctccct ccaagtcgtc accagactct ttagctccgt ctaccctgcg tagcctgaga     600
aaagaaggc tatcgtcccc caaggtccc tctacactaa acccaatatg tcagtcgccc     660
ccagtctctc cccctagatg tgacttcgcc aaccgtagtg tgtaccccc atgggccaca     720
gagtccccga tctacgtggg atcatccagc gatggcgata ctccgccacg ccaaccgcct     780
acatctccca tctccatagg atcatcatcc ccgtctgagg gatcctgggg tgatgacaca     840
gccatgttgg tgctccttgc ggagattgca gaagaagcat ccaagaatga aaagaatgt     900
tccgaaaata atcaggctgg cgaggataat ggggacaacg agattagcaa ggaaagtcag     960
gttgacaagg atgacaatga caataaggat gatgaggagg agcaggagac agatgaggag    1020
gacgaggagg atgacgagga ggatgacgag gaggatgacg aggaggatga cgaggaggat    1080
gacgaggagg atgacgagga ggatgacgag gaggatgacg aggaggatga cgaggaggat    1140
gacgaggagg atgacgagga ggaggacgag gaggaggacg aggaggagga cgaggaggag    1200
gaggacgagg aggatgacga tgatgaggac aatgaggacg aggaggatga cgaggaggag    1260
gacaagaagg aggacgagga ggacgggggc gatggaaaca aaacgttgag catccaaagt    1320
tcacaacagc agcaggagcc acaacagcag gagccacagc agcaggagcc acagcagcag    1380
gagcccctgc aggagccaca acagcaggag ccacagcagc aggagccaca gcagcaggag    1440
cccctgcagg agccacaaca gcaggagcca cagcagcagg agcccctgca ggagccacaa    1500
cagcaggagc acaacagca ggagccacag cagcaggagc cacagcagca ggagccacag    1560
cagcaggagc cacagcagca ggagccacag cagcaggagc cacagcagca ggagccacag    1620
cagcaggagc cacagcagca ggagccacag cagcgggagc cacagcagcg ggagccccag    1680
cagcgggagc cacagcagcg ggagccacag cagcgggagc cacagcagcg ggagccacag    1740
cagcgggagc cacagcagcg ggagccacag cagcgggagc cacagcagca ggatgagcag    1800
cagcaggatg agcagcagca ggatgagcag cagcaggatg agcagcagca ggatgagcag    1860
cagcaggatg agcagcagca ggatgagcag cagcaggatg agcagcagca ggatgagcag    1920
cagcaggatg agcagcagca ggatgagcag cagcaggatg agcagcagca ggatgagcag    1980
cagcaggatg agcagcagca ggatgagcag cagcaggatg agcagcagca ggatgagcag    2040
```

```
cagcaggatg agcagcagca ggatgagcag cagcaggatg agcagcagca ggatgagcag   2100
gagcagcagg atgagcagga gcagcaggat gagcaggagc agcaggatga gcagcagcag   2160
gatgagcagc agcagcagga tgagcagcag cagcaggatg agcagcagca gcaggatgag   2220
cagcagcagc aggatgagca gcagcagcag gatgaacagg agcagcagga ggagcaggag   2280
cagcaggagg agcaggagca ggagttagag gagcaggagc aggagttaga ggatcaggag   2340
caggagttag aggagcagga gcaggagtta gaggagcagg agcaggagtt agaggagcag   2400
gagcaggagt tagaggagca ggagcaggag ttagaggagc aggagcagga gttagaggag   2460
caggagcagg agttagagga gcaggagcag gagttagagg agcaggagca ggagttagag   2520
gagcaggagg tggaagagca agagcaggag gtggaagagc aagagcagga gcaggaagag   2580
caggaattag aggaggtgga ggagcaagag caggagcagg aggagcagga ggagcaggag   2640
ttagaggagg tggaagagca ggaagagcag gagttagagg aggtggaaga gcaggaagag   2700
caggagttag aggaggtgga agagcaggag cagcaggagt tagaggaggt ggaagagcag   2760
gagcagcagg gggtggaaca gcaggagcag gagacggtgg aagagcccat aatcttgcac   2820
gggtcgtcat ccgaggacga aatggaagtg gattaccctg ttgttagcac acatgaacaa   2880
attgccagta gcccaccagg agataataca ccagacgatg acccacaacc tggcccatct   2940
cgcgaatacc gctatgtact cagaacatca ccaccccaca gacctggagt tcgtatgagg   3000
cgcgttccag ttacccaccc aaaaaagcca catccaagat accaacaacc accggtccct   3060
tacagacaga tagatgattg tcctgcgaaa gctaggccac aacacatctt ttatagacgc   3120
tttttgggaa aggatggaag acgagatcca aagtgtcaat ggaagtttgc agtgattttt   3180
tggggcaatg acccatacgg acttaaaaaa ttatctcagg ccttccagtt tggaggagta   3240
aaggcaggcc ccgtgtcctg cttgccccac cctggaccag accagtcgcc cataacttat   3300
tgtgtatatg tgtattgtca gaacaaagac acaagtaaga agtacaaat ggcccgccta   3360 gcctgggaag ctagtcaccc cctggcagga aacctacaat cttccatagt taagtttaaa   3420
aagcccctgc cattaaccca gccagggaa accaaggtc ctgggactc tccacaggaa   3480 atgacataa                                                         3489
```

<210> SEQ ID NO 2
<211> LENGTH: 1162
<212> TYPE: PRT
<213> ORGANISM: Kaposi's sarcoma-associated herpesvirus

<400> SEQUENCE: 2

```
Met Ala Pro Pro Gly Met Arg Leu Arg Ser Gly Arg Ser Thr Gly Ala
 1               5                  10                  15

Pro Leu Thr Arg Gly Ser Cys Arg Lys Arg Asn Arg Ser Pro Glu Arg
            20                  25                  30

Cys Asp Leu Gly Asp Asp Leu His Leu Gln Pro Arg Lys His Val
        35                  40                  45

Ala Asp Ser Ile Asp Gly Arg Glu Cys Gly Pro His Thr Leu Pro Ile
    50                  55                  60

Pro Gly Ser Pro Thr Val Phe Thr Ser Gly Leu Pro Ala Phe Val Ser
65                  70                  75                  80

Ser Pro Thr Leu Pro Val Ala Pro Ile Pro Ser Pro Ala Pro Thr
            85                  90                  95

Pro Leu Pro Pro Pro Ala Leu Leu Pro Pro Val Thr Thr Ser Ser Ser
           100                 105                 110
```

```
Pro Ile Pro Pro Ser His Pro Val Ser Pro Gly Thr Thr Asp Thr His
        115                 120                 125

Ser Pro Ser Pro Ala Leu Pro Pro Thr Gln Ser Pro Glu Ser Ser Gln
        130                 135                 140

Arg Pro Pro Leu Ser Ser Pro Thr Gly Arg Pro Asp Ser Ser Thr Pro
145                 150                 155                 160

Met Arg Pro Pro Ser Gln Gln Thr Thr Pro Pro His Ser Pro Thr
                165                 170                 175

Thr Pro Pro Pro Glu Pro Pro Ser Lys Ser Ser Pro Asp Ser Leu Ala
                180                 185                 190

Pro Ser Thr Leu Arg Ser Leu Arg Lys Arg Arg Leu Ser Ser Pro Gln
        195                 200                 205

Gly Pro Ser Thr Leu Asn Pro Ile Cys Gln Ser Pro Val Ser Pro
        210                 215                 220

Pro Arg Cys Asp Phe Ala Asn Arg Ser Val Tyr Pro Pro Trp Ala Thr
225                 230                 235                 240

Glu Ser Pro Ile Tyr Val Gly Ser Ser Asp Gly Asp Thr Pro Pro
                245                 250                 255

Arg Gln Pro Pro Thr Ser Pro Ile Ser Ile Gly Ser Ser Pro Ser
                260                 265                 270

Glu Gly Ser Trp Gly Asp Asp Thr Ala Met Leu Val Leu Leu Ala Glu
        275                 280                 285

Ile Ala Glu Glu Ala Ser Lys Asn Glu Lys Glu Cys Ser Glu Asn Asn
        290                 295                 300

Gln Ala Gly Glu Asp Asn Gly Asp Asn Glu Ile Ser Lys Glu Ser Gln
305                 310                 315                 320

Val Asp Lys Asp Asp Asn Asp Asn Lys Asp Asp Glu Glu Glu Gln Glu
                325                 330                 335

Thr Asp Glu Glu Asp Glu Glu Asp Asp Glu Glu Asp Asp Glu Glu Asp
                340                 345                 350

Asp Glu Glu Asp Asp Glu Glu Asp Asp Glu Glu Asp Asp Glu Glu Asp
                355                 360                 365

Asp Glu Glu Asp Asp Glu Glu Asp Asp Glu Glu Asp Asp Glu Glu Asp
        370                 375                 380

Asp Glu Glu Glu Asp Glu Glu Glu Asp Glu Glu Asp Glu Glu Glu
385                 390                 395                 400

Glu Asp Glu Glu Asp Asp Asp Glu Asp Asn Glu Asp Glu Glu Asp
                405                 410                 415

Asp Glu Glu Glu Asp Lys Lys Glu Asp Glu Glu Asp Gly Gly Asp Gly
                420                 425                 430

Asn Lys Thr Leu Ser Ile Gln Ser Ser Gln Gln Gln Glu Pro Gln
        435                 440                 445

Gln Gln Glu Pro Gln Gln Gln Glu Pro Gln Gln Gln Glu Pro Leu Gln
        450                 455                 460

Glu Pro Gln Gln Gln Glu Pro Gln Gln Gln Glu Pro Gln Gln Gln Glu
465                 470                 475                 480

Pro Leu Gln Glu Pro Gln Gln Gln Glu Pro Gln Gln Gln Glu Pro Leu
                485                 490                 495

Gln Glu Pro Gln Gln Gln Glu Pro Gln Gln Glu Pro Gln Gln Gln
                500                 505                 510

Glu Pro Gln Gln Gln Glu Pro Gln Gln Gln Glu Pro Gln Gln Gln Glu
        515                 520                 525
```

```
Pro Gln Gln Gln Glu Pro Gln Gln Glu Pro Gln Gln Glu Pro
    530                 535                 540
Gln Gln Gln Glu Pro Gln Arg Glu Pro Gln Gln Arg Glu Pro Gln
545                 550                 555                 560
Gln Arg Glu Pro Gln Gln Arg Glu Pro Gln Gln Arg Glu Pro Gln Gln
                565                 570                 575
Arg Glu Pro Gln Gln Arg Glu Pro Gln Gln Arg Glu Pro Gln Gln Arg
            580                 585                 590
Glu Pro Gln Gln Gln Asp Glu Gln Gln Gln Asp Glu Gln Gln Gln Asp
            595                 600                 605
Glu Gln Gln Gln Asp Glu Gln Gln Gln Asp Glu Gln Gln Gln Asp Glu
    610                 615                 620
Gln Gln Gln Asp Glu Gln Gln Gln Asp Glu Gln Gln Gln Asp Glu Gln
625                 630                 635                 640
Gln Gln Asp Glu Gln Gln Gln Asp Glu Gln Gln Gln Asp Glu Gln Gln
                645                 650                 655
Gln Asp Glu Gln Gln Gln Asp Glu Gln Gln Gln Asp Glu Gln Gln Gln
            660                 665                 670
Asp Glu Gln Gln Asp Glu Gln Gln Gln Asp Glu Gln Gln Gln Asp
            675                 680                 685
Glu Gln Gln Gln Asp Glu Gln Gln Gln Asp Glu Gln Gln Gln Asp
    690                 695                 700
Glu Gln Gln Gln Gln Asp Glu Gln Gln Gln Asp Glu Gln Gln Gln
705                 710                 715                 720
Asp Glu Gln Gln Gln Asp Glu Gln Gln Gln Asp Glu Gln Gln Gln
                725                 730                 735
Gln Gln Asp Glu Gln Gln Gln Asp Glu Gln Gln Gln Gln Asp Glu
            740                 745                 750
Gln Glu Gln Gln Glu Gln Glu Gln Glu Gln Glu Gln Glu Gln Gln Glu
    755                 760                 765
Leu Glu Glu Gln Glu Gln Glu Leu Glu Asp Gln Glu Gln Glu Leu Glu
770                 775                 780
Glu Gln Gln Gln Glu Leu Glu Gln Glu Gln Glu Gln Leu Glu Glu Glu
785                 790                 795                 800
Glu Gln Glu Leu Glu Glu Gln Glu Gln Glu Leu Glu Glu Gln Glu Gln
                805                 810                 815
Glu Leu Glu Glu Gln Glu Gln Glu Leu Glu Gln Glu Gln Glu Leu
            820                 825                 830
Glu Glu Gln Glu Gln Glu Leu Glu Glu Gln Glu Val Glu Glu Gln Glu
    835                 840                 845
Gln Glu Val Glu Glu Gln Glu Gln Glu Gln Glu Gln Glu Leu Glu
850                 855                 860
Glu Val Glu Glu Gln Glu Gln Glu Gln Glu Gln Glu Gln Glu Gln Glu
865                 870                 875                 880
Leu Glu Glu Val Glu Glu Gln Glu Gln Glu Leu Glu Glu Val Glu
                885                 890                 895
Glu Gln Glu Glu Gln Glu Leu Glu Glu Val Glu Glu Gln Glu Gln Gln
            900                 905                 910
Glu Leu Glu Glu Val Glu Glu Gln Gln Gln Gly Val Glu Gln Gln
            915                 920                 925
Glu Gln Glu Thr Val Glu Glu Pro Ile Ile Leu His Gly Ser Ser Ser
    930                 935                 940
Glu Asp Glu Met Glu Val Asp Tyr Pro Val Val Ser Thr His Glu Gln
```

```
                945                 950                 955                 960
Ile Ala Ser Ser Pro Gly Asp Asn Thr Pro Asp Asp Pro Gln
                    965                 970                 975
Pro Gly Pro Ser Arg Glu Tyr Arg Tyr Val Leu Arg Thr Ser Pro Pro
            980                 985                 990
His Arg Pro Gly Val Arg Met Arg Arg Val Pro Val Thr His Pro Lys
        995                 1000                1005
Lys Pro His Pro Arg Tyr Gln Gln Pro Pro Val Pro Tyr Arg Gln Ile
    1010                1015                1020
Asp Asp Cys Pro Ala Lys Ala Arg Pro Gln His Ile Phe Tyr Arg Arg
1025                1030                1035                1040
Phe Leu Gly Lys Asp Gly Arg Arg Asp Pro Lys Cys Gln Trp Lys Phe
            1045                1050                1055
Ala Val Ile Phe Trp Gly Asn Asp Pro Tyr Gly Leu Lys Lys Leu Ser
        1060                1065                1070
Gln Ala Phe Gln Phe Gly Gly Val Lys Ala Gly Pro Val Ser Cys Leu
    1075                1080                1085
Pro His Pro Gly Pro Asp Gln Ser Pro Ile Thr Tyr Cys Val Tyr Val
    1090                1095                1100
Tyr Cys Gln Asn Lys Asp Thr Ser Lys Lys Val Gln Met Ala Arg Leu
1105                1110                1115                1120
Ala Trp Glu Ala Ser His Pro Leu Ala Gly Asn Leu Gln Ser Ser Ile
            1125                1130                1135
Val Lys Phe Lys Lys Pro Leu Pro Leu Thr Gln Pro Gly Glu Asn Gln
        1140                1145                1150
Gly Pro Gly Asp Ser Pro Gln Glu Met Thr
    1155                1160

<210> SEQ ID NO 3
<211> LENGTH: 801
<212> TYPE: DNA
<213> ORGANISM: Kaposi's sarcoma-associated herpesvirus

<400> SEQUENCE: 3
cgtgaacacc ccgcgccccg cgcccccac accgcgccgc ccctcccct cccccgctc        60 gcctcccggc gctgccgcca ggcccggcc ggagccggcc gccgcgggg ggcagggcgc      120 gcccggcggc tccctcgcgg ggcggggac gggggagggg ggcgccgggc cccgcgcgc      180 cgcggcagcg gagcgcgagc gccccgccg ccgccagcg gcggcgcagg ccccggggcc     240
ccgagccccg agcccgccg gggtacgggg ctaggccacg cctactttt tttcgggcg      300 gccccccgac cctctctcgg cccccggtc ccgcggccc gcgcgcgccc ccccgggggg    360
gtaaaacagg ggggggggga tgcggccgcg cggcgcccg cggcggcggc ggcgcttgct    420
ttcgttttct cccgcggccc cccgggcgcg agccgcgcgg cggcggcggg cgccccctcc   480 cccgggggc tcggcggggg gccccctgtc ccgcgcgggg cccgcgaccc ccggcgccgc    540
cgcgccccga tcccgcgggc gccccgcccc cctgccgggg acgccgccgg gcctgcggcg    600
cctcccgccc gggcatgggg ccgcgcgccg cctcagggcc cggcgcggcc ggcgcctggt   660
ccccgccccc gcccgcgggg gaccccgggc agcgagggaa gggggcgccc tctctctact   720
gtgcgaggag tctgggctgc tgtgtgtgag cctgtttggg ggagcctcct cagtgcttgc   780
tacgtggagc cctggacact a                                              801
```

ASSAYS FOR COMPOUNDS THAT MODULATE RHADINO VIRUS LANA ACTION IN TRANS ON A UNIT OF RHADINO VIRUS DNA TO MEDIATE EFFICIENT EPISOME PERSISTENCE

This application is a division of application Ser. No. 09/298,568, filed Apr. 21, 1999, as U.S. Pat. No. 6,322,792 B1, and which is a continuation-in-part of application Ser. No. 60/109,422, filed Nov. 19, 1998.

1. INTRODUCTION

The present invention relates to a class of viruses called rhadino viruses, or gamma-2 herpes viruses. By way of example, but not by way of limitation, one commonly studied rhadino virus is Kaposi's Sarcoma-Associated Herpes Virus (KSHV), which is also known as Human Herpes Virus 8 (HHV8). More specifically, the invention relates to a rhadino virus protein known as LANA and to a segment of rhadino virus DNA known as the rhodino virus cis-acting element (RVCAE). The LANA protein is encoded by open reading frame (ORF) 73 and is expressed in mammalian cells that are latently infected with KSHV.

The present invention relates to the discovery that LANA is necessary and sufficient for the efficient presistence of rhadino virus DNA in mammalian cells. The invention encompasses methods and assays for determining whether a compound of interest can modulate the ability of LANA to enable the efficient persistence of rhadino virus DNA in a mammalian cell, the binding of LANA to rhadino virus RVCAE DNA, the binding of LANA to mammalian chromosomes, or the tethering by LANA of rhadino virus RVCAE DNA to mammalian chromosomes, as well as such compounds themselves. Because persistent rhadino virus infection is linked to diseases such as Kaposi's Sarcoma (KS) and Primary Effusion Lymphoma (PEL), the invention also encompasses methods and assays for determining whether a compound of interest can modulate rhadino virus-associated disease states, including but not limited to KS and PEL, as well as such compounds themselves.

The invention also relates to the discovery that the expression of LANA in mammalian cells along with the presence of RVCAE on a DNA plasmid is sufficient for the efficient maintenance of the plasmid in those cells. The invention additionally encompasses heterologous DNAs that include RVCAE and a desired DNA such that the heterologous DNA effeciently persists as an episome in mammalian cells in which LANA is expressed. The invention also encompasses heterologous DNAs that include RVCAE, a desired DNA, and an expression cassette for LANA, such that the heterologous DNA effeciently persists as an episome in mammalian cells. Because efficient persistance of a heterologous DNA in a mammalian cell is important for gene therapies and related techniques, the invention also encompasses products and methods for gene therapies and related techniques that involve heterologous DNAs having RVCAE and a desired DNA.

The present invention is more fully described below.

2. BACKGROUND OF THE INVENTION

Kaposi's sarcoma (KS) associated herpesvirus (KSHV) or human herpesvirus-8 (HHV-8) likely plays a central role in KS pathogenesis because KSHV seropositivity precedes KS and KSHV DNA is found in almost all KS lesions, whether or not there is coexisting human immunodeficiency virus (HIV) infection (Y. Chang, et al., *Science*, 266, 1865 (1994); P. S. Moore, et al., *J. Virol.*, 70, 549 (1996); S. -J. Gao, et al., *N. Engl. J. Med.*, 335, 233 (1996); P. S. Moore, Y. Chang, *N. Engl. J. Med.*, 332, 1181 (1995)). KSHV is also associated with lymphoproliferative disorders including primary effusion lymphomas (PELs) and multicentric Castleman's disease (E. Cesarman, et al., *Blood*, 86, 2708 (1995); M. B. Rettig, et al., *Science*, 276, 1851 (1997); J. Soulier, et al., *Blood*, 86, 1276 (1995); E. Cesarman, et al., *N. Engl. J. Med.*, 332, 1186 (1995)).

Similar to the gamma-1 herpesvirus Epstein-Barr virus (EBV), KSHV infection in tumor tissue or lymphoma derived cell lines is predominantly latent. Latently infected cells have multiple copies of circularized KSHV DNA maintained as episomes (E. Cesarman, et al., *Blood*, 86, 2708 (1995); M. B. Rettig, et al., *Science*, 276, 1851 (1997); J. Soulier, et al., *Blood*, 86, 1276 (1995); E. Cesarman, Y. Chang, P. S. Moore, J. W. Said, D. M. Knowles, *N. Engl. J. Med.*, 332, 1186 (1995); L. L. Decker, et al., *J. Exp. Med.*, 184, 283 (1996). The EBV EBNA1 protein mediates efficient episome persistence through a cis-acting 1.8 kb EBV DNA sequence termed origin of plasmid replication (oriP) (J. Yates, N. Warren, D. Reisman, B. Sugden, *Proc. Natl. Acad. Sci. USA*, 81, 3806 (1984); J. L. Yates, N. Warren, B. Sugden, *Nature*, 313, 812 (1985); D. R. Rawlins, G. Milman, S. D. Hayward, G. S. Hayward, *Cell*, 42, 859 (1985)). The primate transforming herpes virus saimiri (HVS), which is a rhadino virus, also has a cis-acting sequence that enables efficient persistence of episomes in HVS infected cells (S.-H. Kung, P. G. Medveczky, *J. Virol.*, 70, 1738 (1996)). However, KSHV has no obvious homology to the HVS cis-acting DNA and a trans-acting EBNA1 homolog or analog has not been identified in HVS or other gamma-2 herpesviruses.

KSHV open reading frame (ORF) 73 encodes the latency-associated nuclear antigen (LANA, LNA, or LNA1) which is predicted to be 1162 amino acids and lacks a known function (Y. Chang, et al., *Science*, 266, 1865 (1994); P. S. Moore, et al., *J. Virol.*, 70, 549 (1996); S.-J. Gao, et al., *N. Engl. J. Med.*, 335, 233 (1996); P. S. Moore, Y. Chang, *N. Engl. J. Med.*, 332, 1181 (1995); J. J. Russo, et al., *Proc. Natl. Acad. Sci. USA*, 93, 14862 (1996); P. Kellam, et al., *J. of Human Virol.*, 1, 19 (1997); L. Rainbow, et al., *J. Virol.*, 71, 5915 (1997); D. H. Kedes, M. Lagunoff, R. Renne, D. Ganem, *J. Clin. Invest.*, 100, 2606 (1997); F. Neipel, J. C. Albrecht, B. Fleckenstein, *J. Virol.*, 71, 4187 (1997)). A homologous open reading frame exists in other gamma-2 herpesviruses such as, but not limited to, HV saimiri and MHV68. (J. C. Albrecht, et al., *J. Virol.*, 66, 5047 (1992); H. W. Virgin IV, et al., *J. Virol.*, 71, 5894 (1997)). LANA is reactive with most KSHV-immune sera which detect LANA in KSHV infected PEL cells and KS spindle cells (P. Kellam, et al., *J. of Human Virol.*, 1, 19 (1997); L. Rainbow, et al., *J. Virol.*, 71, 5915 (1997); D. H. Kedes, M. Lagunoff, R. Renne, D. Ganem, *J. Clin. Invest.*, 100, 2606 (1997); F. Neipel, J. C. Albrecht, B. Fleckenstein, *J. Virol.*, 71, 4187 (1997); S. J. Gao, et al., *Nature Medicine*, 2, 925 (1996); D. H. Kedes, et al., *Nature Medicine*, 2, 918 (1996); D. Jones, et al., *N. Engl. J. of Med.*, 339, 444 (1998); R. Renne, et al., *Nature Medicine*, 2, 342 (1996); L. Szekely, et al., *J. of General Virology*, 79, 1445 (1998)).

3. SUMMARY OF THE INVENTION

The present invention encompasses methods and assays for determining whether a compound of interest can modulate the ability of LANA to enable the efficient persistence of rhadino virus in a mammalian cell, the binding of LANA to rhadino virus RVCAE DNA, the binding of LANA to mammalian chromosomes, the tethering by LANA of rhadino virus RVCAE DNA to mammalian chromosomes, or any rhadino virus-associated disease states, including but not limited to KS and PEL, as as well as such compounds themselves. The present invention also encompases products and methods for gene therapies and related techniques involving the use of heterologous DNAs that include the rhadino virus cis-acting element (RVCAE) and a desired DNA such that the heterologous DNA effecintly persists as an episome in mammalian cells in which LANA is expressed, including heterologous DNAs that carry an expression cassette for LANA.

The invention is based, in part, on the discovery that LANA is necessary and sufficient for the efficient presistence of rhadino virus DNA in mammalian cells. The examples described infra provide the first identification of a trans-acting factor that supports episome persistence of gamma-2 herpesvirus DNA. The factor is identified as RVCAE. According to one embodiment of the invention the RVCAE element includes at least one copy of the rhadino virus terminal repeat (TR). According to another embodiment of the invention, the RVCAE element includes at least three copies of the rhadino virus terminal repeat (TR) and 0.6 kb of the rhadino virus adjacent unique DNA.

It is shown that LANA associates with KSHV episomes in interphase and on chromosomes in mitotic cells. Cell lines stably expressing LANA are shown to support episomal persistence of KSHV DNA. LANA is shown to concentrate to dots at sites of KSHV DNA or at sites of artificial episomes that contain the rhadino virus cis-acting element (RVCAE). These findings support a model in which LANA links, or tethers, KSHV DNA to chromosomes during mitosis to ensure efficient segregation of KSHV episomes to progeny cells.

The invention is described in more detail in the following sections and examples for purposes of clarity and not by way of limitation.

3.1 Definitions

As used herein, the following terms and abbreviations shall have the meanings indicated below:

| | |
|---|---|
| basepair(s) | bp |
| kilobasepair(s) | kb |
| deoxyribonucleic acid | DNA |
| Kaposi's Sarcoma-Associated Herpes Virus | KSHV |
| also known as Human Herpes Virus 8 | HHV8 |
| open reading frame | ORF |
| Kaposi's Sarcoma | KS |
| Primary Effusion Lymphoma | PEL |
| human immunodeficiency virus | HIV |
| Epstein-Barr virus | EBV |
| origin of plasmid replication | oriP |
| herpes virus saimiri | HVS |
| latency-associated nuclear antigen | LANA, LNA, or LNA1 |
| FLAG-tagged LANA | F-LANA |
| fluorescent in situ hybridization | FISH |
| polymerase chain reaction | PCR |
| rhadino virus cis-acting element | RVCAE |

As used herein, the word "modulate" (and its derivatives, such as "modulation") shall have its usual meaning, but shall also encompass the meanings of the words "enhance," "mimic," "inhibit," or "prevent" (and their deriviatives).

As used herein, the word "or" is intended to operate in the strictly logical sense. That is, a statement "A or B is true" is logically true if A is true, or B is true, or both A and B are true. Therefore, as used herein, the term "or" shall have the same meaning as the idiomatic expression "and/or."

As used herein, the term "heterologous DNA" is intended to refer to any DNA that is introduced into a cell.

4. BRIEF DESCRIPTION OF THE DRAWINGS

The DNA constructs discussed in these brief descriptions are more fully described in the examples set forth in Sections 6–10, infra.

FIG. 1. LANA COLOCALIZES WITH KSHV EPISOMES.

(Panel A) LANA was detected with KSHV immune serum (green signal), and (Panel B) KSHV episomes were detected by FISH (red signal) in the same BCBL-1 cells. (Panel C) Overlay of Panels A and B results in yellow signal at sites of colocalization. The arrows indicate one site of colocalization. Confocal microscopy was performed with a Zeiss Axioskop, PCM2000 hardware and C-imaging software. (Magnification 630×)

FIG. 2. LANA ASSOCIATES WITH KSHV GENOMES ON CHROMOSOMES.

BCBL-1 cells were metaphase arrested with Colcemid and swollen in hypotonic buffer. (Panel A) KSHV genomes were detected by FISH (red signal), (Panel B) LANA was detected with KSHV-immune serum (green signal), and (Panel C) chromosomes were detected with DAPI (purple signal) (13). The same mitotic cell is shown in Panels A, B, and C. (Panel D) Overlay of panels A, B and C. A white signal results when KSHV genome and LANA colocalize on a chromosome. The arrows indicate one site of colocalization. "I" indicates adjacent interphase nuclei. Staining was detected with a Zeiss Axiovert S100 microscope fitted with Biorad MRC1024/2P confocal hardware, a Multiphoton Tsunami Laser and Biorad Lasersharp 3.1 software. (Magnification 630×)

FIG. 3. LANA CONCENTRATES TO DOTS WITH Z6 KSHV DNA.

(Panels A and C) BJAB/F-LANA cells and (Panels B and D) BJAB/F-LANA cells transfected with Z6 were stained with propidium iodide (red signal) to detect interphase nuclei (Panels A, B) or metaphase chromosomes (Panels C, D) and KSHV immune serum (green signal) to visualize LANA. Colocalization of nucleic acid and LANA results in yellow signal. Confocal microscopy was performed as in FIG. 1. (Magnification 630×)

Figure 4:
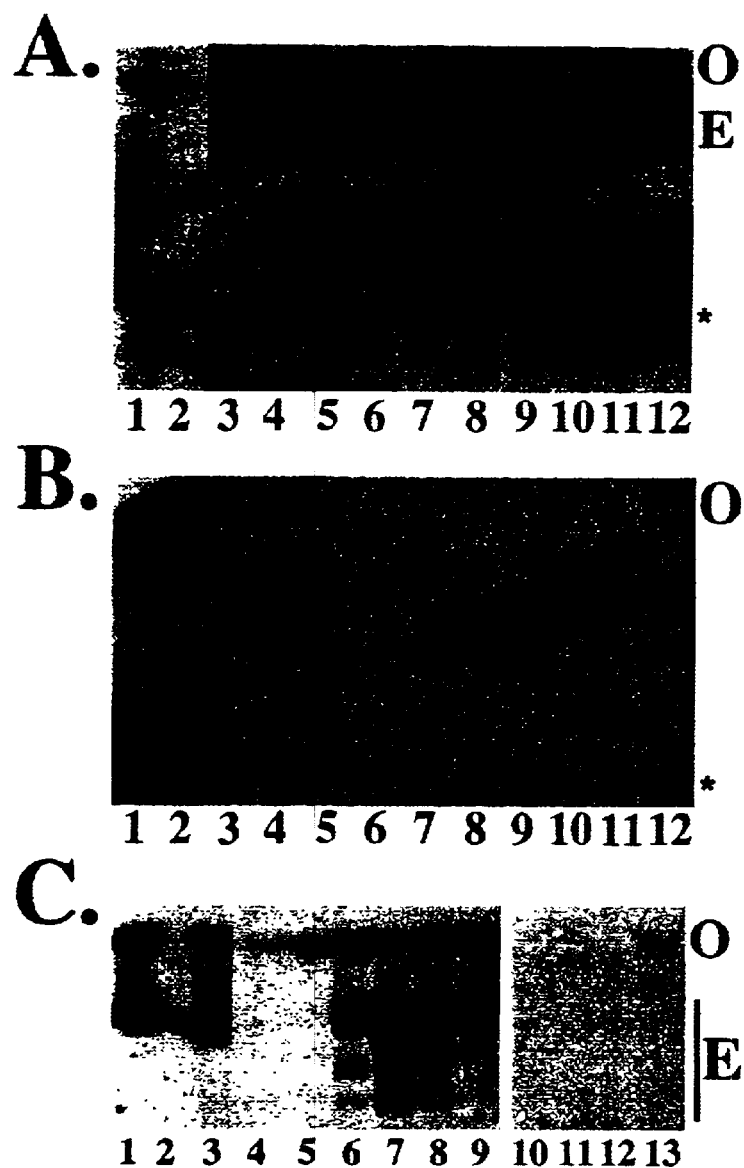

FIG. 4. LANA AND F-LANA MEDIATE EPISOMAL PERSISTENCE OF Z6 AND Z6-13 BUT NOT Z8 OR Z6-7 KSHV DNA.

BJAB/LANA cells or BJAB/F-LANA cells were transfected with Z6, Z8, Z6-7 or Z6-13 KSHV DNA, and G418-resistant cell lines selected. Cells ($2 \times 10^6$) were lysed in situ in wells of Gardella gels, electrophoresis performed, and DNA transferred to a nylon membrane (Gardella gels were prepared as described in T. Gardella, P. Medveczky, T. Sairenji, C. Mulder, J. of Virol., 50, 248 (1984)). KSHV DNA was detected with $^{32}$p-labeled (Panel A) Z6, (Panel B) Z8, and (Panel C) Z6-13 (lanes 1–9) or Z6-7 (lanes 10–13) probe. Signals were captured with a Molecular Dynamics PhosphorImager and analyzed with ImageQuant software. In (Panel A), the lanes are designated as follows:
  lane 1, BCBL-1;
  lane 2, Raji (KSHV negative, EBV positive);
  lanes 3–7, Z6 transfected and G418 resistant BJAB/LANA cells; and
  lanes 8–12, Z6-transfected and G418-resistant BJAB/F-LANA cells.

The electrophoretic mobility of Z6 episomes is slower than predicted by size. In (Panel B), lanes are designated as follows:
- lane 1, Raji;
- lane 2, BC-1;
- lane 3, BJAB;
- lane 4, BCBL-1; and
- lanes 5–12, Z8-transfected and G418-resistant BJAB/F-LANA cells.

In (Panel C), lanes are designated as follows:
- lane 1, BC-1;
- lane 2, BJAB;
- Lane 3, BCBL-1;
- lanes 4 and 5, Z6-13-transfected and G418-resistant BJAB cells;
- lanes 6–9, Z6-13-transfected and G418-resistant BJAB/F-LANA cells;
- lanes 10–11, Z6-7-transfected and G418-resistant BJAB cells; and
- lanes 12–13, Z6-7-transfected and G418-resistant BJAB/F-LANA cells.

Multiple episomal bands present in Lanes 6–9 (Panel C) are likely due to duplications and deletions in the terminal repeats as demonstrated by Southern analysis. The BC-1 genome differs in size from that of BCBL-1 (Y. Chang, et al., *Science*, 266, 1865 (1994); P. S. Moore, et al., *J. Virol.*, 70, 549 (1996); S. -J. Gao, et al., *N. Engl. J. Med.*, 335, 233 (1996); P. S. Moore, Y. Chang, *N. Engl. J. Med.*, 332, 1181 (1995); R. Renne, M. Lagunoff, W. Zhong, D. Ganem, *J. Virol.*, 70, 8151 (1996)). The figure is more fully described as follows:
- O denotes well origins;
- E denotes episomes;
- * denotes nicked, degraded, and linear DNA.

FIG. 5. F-LANA MEDIATES EPISOMAL PERSISTENCE OF Z6-U8TRU, Z6-3TRU AND Z6-1TR.

BJAB/F-LANA cells were transfected with Z6-U8TRU, Z6-3TRU, or Z6-1TR KSHV DNA, and G418-resistant cell lines were selected. Cells were lysed in situ in wells of Gardella gels, electrophoresis was performed, and DNA was transferred to a nylon membrane. KSHV DNA was detected with a $^{32}$-p labeled probe corresponding to a 6.5 kB TaqI fragment of Z6-13 KSHV DNA. Signals were captured with a Molecular Dynamics Phosphorimager and analyzed with ImageQuant software. The lanes are designated as follows:
- lane 1, BCBL-1;
- lane 2, BJAB;
- lanes 3–5, Z6-U8TRU transfected and G418-resistant BJAB cells; lanes 6–9, Z6-U8TRU transfected and G418-resistant F-LANA/BJAB cells;
- lanes 10–12, Z6-3TRU transfected and G418-resistant BJAB cells;
- lanes 13–16, Z6-3TRU transfected and G418-resistant F-LANA/BJAB cells;
- lanes 17 and 18, Z6-1TR transfected and G418-resistant BJAB cells;
- lanes 19 and 20, Z6-1 TR transfected and G418-resistant F-LANA/BJAB cells;
- lane 21, 22, and 23 are Z6-U8TRU, Z6-3TRU and Z6-1TR plasmids respectively.

Z6-1TR episomal DNA is larger than Z6-1TR plasmid DNA. The figure is more fully described as follows:
- ● denotes Z6-1TR episomal DNA in lanes 19, 20 and Z6-1TR plasmid DNA in lane 23;
- * denotes Z6-3TRU episomal DNA in lanes 13–16 and plasmid Z6-3TRU in lane 22;
- — denotes Z6-U8TRU episomal DNA in lanes 6–9 and plasmid Z6-U8TRU DNA in lane 21;
- o denotes well origins.

FIG. 6. LANA NUCLEOTIDE SEQUENCE.

The LANA nucleotide sequence as described in Russo et al., *Proc. Natl. Acad. Sci. USA*, 93, 14862–14867 (1996). Variations in LANA sequence have been reported (Kellam et al., *J. of Human Virology*, 1, 19–29 (1997)), and are within the scope of the LANA sequences of the invention, SEQ ID NO: 1.

FIG. 7. LANA PROTEIN SEQUENCE.

The LANA protein sequence as described in Russo et al., *Proc. Natl. Acad. Sci. USA*, 93, 14862–14867 (1996). Variations in LANA sequence have been reported (Kellam et al., *J. of Human Virology*, 1, 19–29 (1997)), and are within the scope of the LANA sequences of the invention, SEQ ID NO: 2.

FIG. 8. SEQUENCE OF THE KSHV TERMINAL REPEAT (TR) UNIT.

The sequence of the KSHV terminal repeat (TR) unit as described in Russo et al., *Proc. Natl. Acad. Sci. USA*, 93, 14862–14867 (1996), SEQ ID NO: 3. Some variability in reports of TR sequence has been noted (Lagunoff et al., *Virology*, 236 (1997).

5. DETAILED DESCRIPTION OF THE INVENTION

Latent infection has a key role in the ability of Herpes Viruses to persist in individuals and in their host species. In primary virus infection, Herpes viruses usually initially replicate in epithelial cells. They then infect and establish latent infection in some internal tissue. In latently infected cells, the viral genome persists in the nucleus as a covalently closed circular episome. An episome is a non-chromosomal, stable DNA element. Persistence as an episome is essential for the ability of the virus to subsequently reactivate from latent infection, in part because lytic Herpes virus DNA replication can only proceed from a circular episomal viral DNA. In natural infection with any Herpes virus, a small number of latently infected cells periodically become permissive for virus replication. Lytic virus infection ensues in those cells, enabling the virus to get back to an epithelial surface. At the epithelial surface, the virus is amplified through lytic replication in epithelial cells and can spread to infect a non immune host, enabling the virus to persist in the surrounding population.

Much of the disease that we associate with Herpes virus infection in individuals is a consequence of latent infection or reactivation from latent infection. Latency infection is particularly important in the pathogenesis of gamma Herpes virus infections. Latent infection with these viruses can result in malignancies. Epstein-Barr virus (EBV) is the prototype human gamma-1 or lymphocrypto Herpes virus and has been studied intensively for the past 35 years. EBV establishes latent infection in lymphocytes and that infection is associated with lymphoid malignancies. The virus can also rarely establish latent infection in epithelial cells and latently infected epithelial cells are found in nasopharyngeal cancer and in some gastric cancers. In almost all latently infected cells, the EBV genome exists as a multi-copy, covalently closed, circular episome. The episome is replicated by the cellular DNA polymerase during S phase. Partitioning to progeny cells during mitosis requires an EBV encoded nuclear antigen protein, EBNA-1. EBNA-1 binds directly to multiple copies of its cognate sequence that are present at a site in the EBV genome and also binds diffusely to chromosomes. By binding to both EBV DNA episomes and to chromosomes, EBNA-1 is believed to assure the persistence of EBV DNA in the post-mitotic cell nucleus. The 2 kb EBV DNA sequence that includes 20 copies of a 30 bp sequence, each of which is the cognate sequence for 2 EBNA-1 molecules, 1 kb of intervening sequence, and a dyad symmetry with 4 EBNA-1 binding sites has been termed oriP because it is a sufficient cis acting element when included in any covalently closed circular plasmid to assure the efficient replication and persistence of that plasmid in human cells that express EBNA-1. Such orip containing plasmids can replicate in the cell nucleus in the absence of EBNA-1 but stringently require EBNA-1 for their persistence in cells over multiple rounds of cell division, consistent with the putative role of EBNA-1 as a linker between orip and chromosomes during mitosis. The EBNA-1/oriP system is frequently used a method to achieve non-chromosomal persistence of a plasmid DNA in human cells. EBNA-1 biding to the 20 copies of the 30 bp repeat also enhances expression from such plasmids. The EBNA-1/oriP system does not convey episome maintenance in most non-primate mammalian cells.

Human Herpes Virus 8 (also known as Kaposils Sarcoma Herpes Virus or KSHV) is a gamma-2 or rhadino Herpes virus. Rhadino Herpes viruses persist in mammalian hosts primarily in a latent form in which the virus DNA is a circular episome in infected cells. In the latent, episomal form of infection, relatively few viral genes are expressed, in contrast to lytic infection in which the virus expresses most of its genes to produce many copies of linear copies of viral DNA which are packaged into virus particles. The Rhadino virus genes expressed in the episomal, latent form of infection are capable of contributing to malignancy and other associated diseases. For instance, after initial infection of mice by the intranasal route, murine herpesvirus 68 (MHV 68) causes a productive (lytic) infection in the lung followed by a latent infection of lymphocytes (Ehtisham et al., *J Virol*, 67, 5247–52 (1993)). After a period of months, murine herpesvirus 68 can cause lymphoproliferative disease (Sunil-Chandra et al., *Am J Pathol*, 145, 818–26 (1994)). The Rhadino virus herpesvirus saimiri (HVS) is naturally found in the New World primate squirrel monkey, in which it does not cause any known 15 disease (Melendez et al., *Lab Anim Care*, 18, 374–81 (1968)). However, HVS infection of other New World primates or New Zealand White rabbits results in T cell lymphoproliferative disease (Daniel et al., *J Natl Cancer Inst*, 53, 1803–7 (1974); Melendez et al., *Lab Anim Care*, 19, 378–86 (1969)). In addition, HVS can infect and immortalize primary (isolated from blood) human T cells in vitro (Biesinger et al., *Proc Natl Acad Sci USA*, 89, 3116–9 (1992); Medveczky et al., *Virology*, 196, 402–12 (1993)). The immortalized T cells contain the episomal form of HVS DNA in multiple copies per cell.

KSHV was discovered in 1994 after its detection in a KS lesion of an HIV infected patient (Chang et al., *Science*, 266, 1865–9 (1994)). Epidemiological studies of KSHV have subsequently shown that it is sexually transmitted among homosexual men (Martin et al., *N Engl J Med*, 338, 948–54 (1998)). However, other means of transmission are also likely since clustering of seropositive individuals occurs within families (Angeloni et al., *J Infect Dis*, 177, 1715–8 (1998)). Furthermore, in Africa where the seroprevalence is much higher than in the U.S.A., children become infected at a young age. In the U.S.A., seropositivity for KSHV is ~25–50% in human immunodeficiency virus (HIV) positive gay men, but less than 10% in the rest of the population (Blauvelt et al., *J Infect Dis*, 176, 771–4 (1997); Chandran et al., *Virology*, 243, 208–17 (1998); Gao et al., *Nat Med*, 2, 925–8 (1996); Kedes et al., *Jama*, 277, 478–81.(1997); Kedes et al., *Nat Med*, 2, 918–24 (1996); Lennette et al., *Lancet*, 348, 858–61 (1996); Martin et al., *N Engl J Med*, 338, 948–54 (1998); Simpson et al., *Lancet*, 348, 1133–8 (1996)). In Italy and Africa, where KS is more common in non-immunosuppressed individuals than in the U.S.A., KSHV seropositivity in the general population is higher, ranging from ~25% in Italy to ~50% in Uganda (Angeloni et al., *J Infect Dis*, 177, 1715–8 (1998); Gao et al., *Nat Med*, 2, 925–8 (1996); Simpson et al., Lancet, 348, 1133–8 (1996)). No primary infection clinical syndrome is yet clearly linked to KSHV.

KSHV is linked to KS, primary effusion lymphomas (PELs) and multicentric Castleman's disease, an aggressive lymphoproliferative disorder. KSHV DNA is found in almost all KS tumors in both HIV positive and HIV negative individuals (Chang et al., *Arch Intern Med*, 156, 202–4 (1996); Foreman et al., *J Clin Invest*, 99, 2971–8 (1997); Miller et al., *N Engl J Med*, 334, 1292–7 (1996); Moore et al., *Aids*, 10, 175–80 (1996)). Further evidence linking KSHV to KS is serologic evidence demonstrating that KSHV infection precedes the development of KS (Gao et al., *N Engl J Med*, 335, 233–41 (1996)). KSHV DNA is also universally found in PELs (Cesarman et al., *N Engl J Med*, 332, 1186–91 (1995); Foreman et al., *J Clin Invest*, 99, 2971–8 (1997); Jones et al., *New England Journal of Medicine*, 339, 444–449 (1998); Said et al., *Blood*, 88, 3124–8 (1996)). These tumors grow in body cavity effusions in HIV positive and HIV negative immunosuppressed individuals. PELs may be infected only with KSHV or coinfected with Epstein-Barr virus (EBV), a related herpesvirus. The malignant cells in PELs lack most B or T cell markers but have characteristics of mature B or plasmacytoid cells. KSHV DNA is consistently found in HIV positive associated multicentric Castleman's disease and in ~40% of cases in HIV negative patients (Kikuta et al., *Br J Haematol*, 99, 790–3 (1997); Soulier et al., *Blood*, 86, 1276–80 (1995)). A common factor for all these disorders is their tendency to occur most commonly and in more severe forms in immunosuppressed individuals.

Similar to EBV, KSHV primarily exists in a latent state as a multiple copy, circular, extrachromasomal episome in infected tumor cells (Decker et al., *J Exp Med*, 184, 283–8 (1996); Miller et al.,*J Virol*, 71, 314–24 (1997); Renne et al., *Nat Med*, 2, 342–6 (1996); Staskus et al.,*J Virol*, 71, 715–9 (1997); Sturzl et al., *Int J Cancer*, 72, 68–71 (1997); Zhong et al., *Proc Natl Acad Sci USA*, 93, 6641–6 (1996)). Only a few percent of KS tumor cells or cells in PEL derived cell lines contain KSHV undergoing lytic infection. Therefore, almost all KSHV infected cells contain multiple copies of episomes. As cells multiply through cell division, the episomes must also multiply and efficiently distribute to progeny cells in order for the episomes to efficiently persist. Therefore, efficient persistence indicates maintenance of episomes in a cell population regardless of the number of cell divisions. The circularized episomes must replicate and segregate to progeny cells to efficiently persist, but this aspect of KSHV infection had not been previously investigated. The only previous potential model system for such persistence is the EBV EBNA-1 protein described above, which mediates persistence of EBV episomes 10 through a cis-acting ~2 kb DNA sequence termed origin of plasmid replication (orip) (Gahn and Sugden, *J Virol*, 69, 2633–6

(1995)). Multiple EBNA-1 binding sites are present in repeat elements in oriP (Lupton and Levine, *Molecular and Cellular Biology*, 5, 2533–2542 (1985); Platt et al., *J Virol*, 67, 1739–45 (1993); Yates et al., *Proc Natl Acad Sci USA*, 81, 3806–10 (1984)). Also, the more closely related HVS has a cis-acting sequence that enables efficient persistence of episomes in HVS infected cells (Kung and Medveczky, *Journal of Virology*, 70, 1738–17444 (1996)). However, KSHV has no obvious homology to the HVS cis-acting DNA and a trans-acting EBNA-1 homolog or analog has not been identified in HVS or any other gamma-2 herpesvirus.

By analogy with EBV, the KSHV genes expressed in latent infection likely play central roles in tumorigenesis. However, this does not exclude potential tumorigenic roles of genes expressed during lytic replication. In latently infected cells, KSHV expresses a limited number of genes (Moore et al., *Science*, 274, 1739–44 (1996); Rainbow et al., *J Virol*, 71, 5915–21 (1997); Staskus et al., *J Virol*, 71, 715–9 (1997); Sturzl et al., *Int J Cancer*, 72, 68–71 (1997); Zhong et al., *Proc Natl Acad Sci USA*, 93, 6641–6 (1996)). Cell homologs which are expressed in KSHV latent infection include the cyclin D gene and the FLICE inhibitory protein (Sarid et al., *J Virol*, 72, 1005–12 (1998)). The interleukin-6 homolog is expressed in latent infection only in lymphoid cells and not KS. Two KSHV genes without homology to known proteins are also expressed in latent infection. The T0.7 transcript encodes the K12 ORF which exerts transforming effects in Rat-3 rodent fibroblasts and causes them to be tumorigenic in nude mice (Muralidhar et al., *J Virol*, 72, 4980–8 (1998); Staskus et al., *J Virol*, 71, 715–9 (1997)). The latency-associated nuclear antigen (LANA or LNA) is also expressed in latent infection.

The latency-associated nuclear antigen (LANA, LNA or LNA1) was initially detected by indirect immunofluorescent microscopy performed on KSHV infected PEL cell lines with serum from KSHV infected individuals. Such serum reveals punctate nuclear staining for which the reactive antigen has been mapped to KSHV ORF73 at the right end of the KSHV genome (Kedes et al., *J Clin Invest*, 100, 2606–10 (1997); Kellam et al., *Journal of Human Virology*, 1, 19–29 (1997); Rainbow et al., *J Virol*, 71, 5915–21 (1997)). The ORF73 transcript is spliced once upstream of ORF73 and also contains the ORFs for the cyclin D2 homolog and FLICE inhibitory protein located downstream of ORF73. ORF73 encodes a predicted 1162 amino acid protein without homology to known proteins and immunoreactive serum detects LANA as a 222 and 234 kd doublet on immunoblot (Gao et al., *N Engl J Med*, 335, 233–41 (1996)).

The invention is described in further detail in the following subsections and examples for purposes of clarity and not by way of limitation.

The experiments described in the examples in sections 6–10, infra, were conducted to determine whether LANA is similar to EBNA-1 in being a protein involved in KSHV episome maintenance. (LANA could be similar to any of the five other EBV nuclear proteins expressed in latent EBV infection. These other EBNAs do not mediate episome maintenance but are involved in regulating transcription. Alternatively, LANA could be functionally distinct from any EBNA.) We found that LANA is similar to EBNA-1 in associating with human chromosomes in KSHV infected PEL cells and in human B lymphoblasts that are not KSHV infected. In human B lymphocytes that are not KSHV infected, LANA distribution was diffuse on mitotic chromosomes, quite similar to EBNA-1. However, in KSHV infected PEL cells, LANA accumulated in dots on chromosomes, whereas EBNA-1 is diffuse on chromosomes of EBV infected cells. This difference turned out to be due to the effect of the presence of KSHV DNA in cells. Even though LANA differed from EBNA-1 in its distribution in infected cells, the LANA dots localized to sites of KSHV episomes on the chromosomes of PEL cells, consistent with our initial hypothesis that LANA has a tethering function of tying KSHV DNA episomes to chromosomes. A search was conducted to determine whether KSHV DNA has a cis acting element that would enable LANA to recognize KSHV DNA so as to tether it to chromosomes. Indeed, LANA seemed to associate with KSHV DNA even more than EBNA-1 does with EBV DNA. We proceeded to look for a KSHV DNA sequence that enabled plasmids containing a selectable marker to efficiently persist as episomes in LANA expressing cells. We identified a KSHV cosmid DNA fragment, Z6, that contains such a sequence. From this cosmid we succeeded in sub cloning a 3 kbp DNA sequence consisting of 3 copies of the KSHV terminal repeat and 0.6 kb of partially unique DNA. This Rhadino virus cis acting element (RVCAE) enables a plasmid containing it and a positive selection marker expression cassette to efficiently persist as an episome in LANA positive cells and to express the positive selection marker. Indeed, the persisting plasmid episome in cells was identical in electrophoretic mobility to the input DNA. A smaller cis acting element consisting of only a single copy of the KSHV terminal repeat appears to have much of the RVCAE activity in enabling episome persistence in LANA expressing cells and expression of a positive selection marker from the episomal DNA. RVCAEs of all sizes required LANA for their efficient persistence in cells. Thus, we have discovered that LANA is necessary and sufficient and necessary for the episomal persistence of RVCAE DNA and covalently linked plasmid DNA (including the KSHV genome) in mammalian cells. This discovery has two important types of applications. First, from the identification of the two essential components, LANA and RVCAE, by which KSHV DNA is maintained in cells we can devise assays that are evident to those familiar with the state of the art (described for the purposes of example but not for limitation below), so as to screen for and identify molecules that could inhibit LANA interaction with the RVCAE in cells. Molecules so identified would be useful as lead compound for the development of drugs to eliminate latent KSHV infection in humans. The elimination of latent KSHV infection would be useful for the prevention or treatment of KSHV associated diseases described above. Such molecules could include but are not limited to small molcules, ribozymes, antisense oligonucleotides or polynuceotides, peptides, or proteins. Second, LANA expression and RVCAE can be used to enable the efficient persistence as an episome of plasmid DNA covalently linked to RVCAE in mammalian cells. There is a need for systems that mediate efficient episome maintenance for various kinds of gene transfer experiments. Episome maintenance is superior to chromosomal insertion since chromosomal insertion can result in the gene transferred DNA disrupting or altering cell gene expression and the adjacent cell DNA frequently alter transcription of the transferred DNA. Episome maintainence is also more efficient for the immediate establishment of residence and transferred gene expression. Currently, EBNA-1 and oriP are the preferred method for enabling episome persistence. EBNA-1 and oriP are restricted in their effect to human cells. Rhadinoviruses typically have a broader host range than lymphocrytiviruses. KSHV ORF73 (LANA) and the KSHV RVCAE are likely to function more broadly in mammalian cell types. In addition, similar Rhadino viruses exist in many other mammalian species including but not limited to rodents, equine, new world and old world primates. As described above, these rhadino viruses also ORF73s and multi-copy TRs that are homologous to KSHV DNA. These homologous DNAs are likely to constitute efficient episome maintenance components when used as we have used KSHV LANA and RVCAE. One method for enabling plasmid persistence as a stable episome in mammalian cells is to include a LANA expression cassette and the RVCAE on a plasmid. Such a plasmid could include DNA for positive selection, DNA for RNA expression for the purposes of a ribozyme or antisense RNA or for sense RNA so as to translate a protein, or DNA for tissues specific or regulated expression of an RNA. The plasmid could be delivered into cells in culture for various experimental or therapeutic purposes or could be delivered into mammals for preventative or therapeutic purposes. The vehicles for delivery could include gene gun, liposomes, or viral vectors. All of the previous are examples of uses but are not intended to be limiting.

5.1. Lana Genes and Gene Products

The LANA gene products of the present invention include, but are not limited to, LANA peptides, polypeptides, polypeptide fragments, and fusion proteins as described herein. The LANA genes of the present invention include LANA nucleic acid molecules as described herein as well as deletions and substitutions thereof.

In one embodiment, such LANA genes and gene products are from a mammalian, and prefereably human or primate, rhadino virus. In one embodiment, such genes and gene products are naturally ocurring. Such embodiments may be exclusive or overlapping.

It is well within the skill of one in the art to purify and sequence the LANA gene products and to clone the LANA DNA's; and such procedures may be conducted, for example, as described in P. Kellam, et al., *J. of Human Virol.*, 1, 19 (1997); L. Rainbow, et al., *J. Virol.*, 71, 5915 (1997); D. H. Kedes, et al., *J. Clin. Invest.*, 100, 2606 (1997). The sequence of KSHV open reading frame (ORF) 73, which encodes for LANA, (Cesarman et al., *J. Virol.*, 70, 8218–23 (1996); Russo et al., *Proc. Natl. Acad. Sci. USA*, 93, 14862–14867 (1996))(Genbank accession number U75698) (long unique KSHV sequence); and (Neipel et al., *J. Virol.*, 71, 4187–92 (1997)) (Genbank accession number U93872) has homology to ORF 73 of herpesvirus saimiri (Albrecht, *J. Virol.*, 66, 5047–5058 (1992)). Murine herpesvirus 68 (Virgin et al., *J. Virol.*, 71, 5894–904 (1997)) (Genbank accession number GAMMAHV U97553) and other herpesviruses, including other primate herpesviruses also have ORF 73 homologs. KSHV latency-associated nuclear antigen (LANA, LNA, LNA1) was mapped to ORF 73 (Kedes et al., *J. Clin. Invest.*, 100, 2606–10 (1997); Kellam et al., *Journal of Human Virology*, 1, 19–29 (1997); Rainbow et al., *Journal of Virology*, 71, 5915–5921 (1997)).

The LANA gene products of the invention include, but are not limited to, gene products containing the amino acid sequence set forth in FIG. 7, supra, SEQ ID NO: 2 as well as the amino acid sequence of of at least one of the domains or subdomains as described infra. That is, in addition to full length LANA gene products, LANA polypeptide fragments are also included within the scope of the invention. In this sense, the term "LANA polypeptide fragments" encompasses polypeptides that comprise LANA fragments and deletions, including internal deletions or any combination of LANA fragments or deletions. In particular, the LANA polypeptides of the invention include those that specifically include or lack any of the domains or subdomains described infra, or any combination thereof.

Two potential nuclear localization signals (NLS) are present in the LANA N-terminus. One NLS is present between codons 40 and 50 and another is present between codons 190 and 210. The LANA C-terminus is capable of nuclear localization, despite lacking as strong concensus NLS's as present in the LANA N-terminus (Kellam et al., *Journal of Human Virology*, 1, 19–29 (1997)). Codons 320–430 contain a highly acidic repeat region, consisting almost exclusively of aspartic acid and glutamic acid between codons 330–430. This region is even more acidic than the VP16 or EBV EBNA2 transactivating domains and lacks the interspersed hydrophobic residues present in these transactivating domains. Codons 430–760 encode glutamine rich repeat elements which can be separated into three domains. Codons 430–550 contain repeat elements consisting of glutamine, glutamic acid, and proline. Codons 550–590 contain repeat elements consisiting of glutamine, glutamic acid, proline and arginine. Codons 590–760 contain repeat elements made up (exclusively from codons 595–750) of glutamine, glutamic acid, and aspartic acid. Codons 760–840 consist almost entirely of a glutamic acid and glutamine rich potential leucine zipper. This region is likely to mediate protein-protein interactions. The C-terminal ~300 LANA amino acids are largely non-repeated (or unique) sequence and are reactive with human sera. The LANA polypeptides of the present invention include any one of these domains, any subdomain of these domains and any combination of these domains or subdomains.

A tethering function for LANA would require simultaneous association between LANA and both KSHV DNA and chromosomes. LANA association with DNA is likely to be through a basic LANA domain due to the negative charge of DNA. LANA alternatively may interact indirectly with KSHV DNA through a KSHV DNA binding protein. LANA likely interacts with chromosomes through a protein-protein associaion although other possibilities exist, such as LANA interacting directly with chromosomal nucleic acid. A possible candidate for LANA's interaction with chromosomes is histone H1. Hi but not H2 or H3 are reported to interact with LANA (J. Wiezorek, et al., First Annual Meeting on Kaposi's sarcoma-associated herpesvirus and related Agents Univ. of Calif., Santa Cruz, July 25–28, (1998)).

Since HVS and other gamma-2 herpesviruses have LANA homologs, these proteins are likely candidates to mediate episome persistence for their respective viral genomes and are within the scope of the LANA polypeptides of the present invention. Gamma-2 herpesvirus LANA type proteins are likely to share the EBNA1 property of transcriptional activation (D. Reisman, B. Sugden, *Molecular and Cellular Biology*, 6, 3838 (1986)).

In a further embodiment of the invention, the LANA DNA or a modified sequence thereof may be ligated to a heterologous sequence to encode a LANA fusion protein. For example, for screening peptide libraries it may be useful to encode a chimeric LANA protein expressing a heterologous epitope that is recognized by a commercially available antibody. A fusion protein may also be engineered to contain a cleavage site located between the LANA sequence and the heterologous protein sequence, so that the LANA protein or protein fragment can be cleaved away from the heterologous moiety. In another embodiment, DNA sequences encoding a fusion protein comprising all or a portion of the LANA protein fused to another protein with a desired activity are within the scope of the invention; e.g., green fluorescent protein, or enzymes such as GUS (β-glucuronidase), β-galactosidase, luciferase, etc.

With respect to nucleic acid molecules, the invention contemplates nucleic acid molecules containing: 1) any DNA sequence that encodes the same amino acid sequence as encoded by the DNA sequences shown in FIG. 6, SEQ ID NO: 1; 2) any DNA sequence that hybridizes to the complement of the coding sequences disclosed herein under highly stringent conditions, e.g., washing in 0.1×SSC/0.1% SDS at 68° C. (Ausubel, et al., eds., 1989, Current Protocols in Molecular Biology, Vol. I, Green Publishing Associates, Inc., and John Wiley & sons, Inc., New York, at p. 2.10.3; see also Sambrook, J. et al., (1989) Molecular cloning, Colo. Spring harbor Press, USA, pp. 9.47–9.55), and which can encode a functionally equivalent gene product; or 3) any DNA sequence that hybridizes to the complement of the coding sequences disclosed therein under less stringent conditions, such as moderately stringent conditions, e.g., washing in 0.2×SSC/0.1% SDS at 42° C. (Ausubel, et al., 1989, supra; Sambrook, et al., 1989, supra), yet which encodes a functionally equivalent gene product.

As used herein, the term "functionally equivalent gene product" refers to a gene product that exhibits at least one of the biological functions of the gene product depicted in FIG. 7, SEQ ID NO: 2. Such biological functions can include, but are not limited to, a function (e.g., a protein-protein interaction function) as exhibited by at least one of the domains of the FIG. 6, SEQ ID NO: 1 gene products.

In another embodiment, DNAs that encode mutant forms of LANA are also included within the scope of the invention. Such mutant LANA DNA sequences encompass deletions, additions and/or substitutions of nucleotide residues, or of regions coding for domains within the LANA protein. These mutated LANA (ORF 73) DNAs may encode gene products that are 25 functionally equivalent or which display properties very different from the native forms of LANA.

The invention also encompasses 1) DNA vectors that contain any of the coding sequences disclosed herein (see FIG. 6), SEQ ID NO: 1, or their complements (i.e., antisense); 2) DNA expression vectors that contain any of the coding sequences disclosed herein, and/or their complements (i.e., antisense), operatively associated with a regulatory element that directs the expression of the coding and/or antisense sequences; and 3) genetically engineered host cells that contain any of the coding sequences disclosed therein, and/or their complements (i.e., antisense), operatively associated with a regulatory element that directs the expression of the coding and/or antisense sequences in the host cell. Regulatory element includes but is not limited to inducible and non-inducible promoters, enhancers, operators and other elements known to those skilled in the art that drive and regulate expression. The invention includes fragments of any of the DNA sequences disclosed herein.

As used herein, the term "recombinant DNA sequence" refers to a DNA sequence that has been derived or isolated from any source, that may be subsequently chemically altered, and later introduced into mammalian cells. An example of a recombinant DNA sequence "derived" from a source, would be DNA sequence that is identified as a useful fragment within a given organism, and which is then chemically synthesized in essentially pure form. An example of such DNA sequence "isolated" from a source would be a DNA sequence that is excised or removed from said source by chemical means, e.g., by the use of restriction endonucleases, so that it can be further manipulated, e.g., amplified, for use in the invention, by the methodology of genetic engineering.

Therefore, "recombinant DNA sequence" includes completely synthetic DNA, semi-synthetic DNA, DNA isolated from biological sources, and DNA derived from introduced RNA. Generally, the recombinant DNA sequence is not originally resident in the genotype which is the recipient of the DNA sequence, or it is resident in the genotype but is not expressed.

The isolated recombinant DNA sequence used for transformation herein may be circular or linear, double-stranded or single-stranded. Generally, the DNA sequence is chimeric linear DNA, or is a plasmid or viral expression vector, that can also contain coding regions flanked by regulatory sequences which promote the expression of the recombinant DNA present in the resultant cell line. For example, the recombinant DNA sequence itself comprise or consist of a promoter that is active in mammalian cells, or may utilize a promoter already present in the genotype that is the transformation target. Such promoters include, but are not limited to, the CMV promoter, SV 40 late promoter and retroviral LTRs (long terminal repeat elements).

The general methods for constructing recombinant DNA which can transform target cells are well known to those skilled in the art, and the same compositions and methods of construction may be utilized to produce the DNA useful herein. For example, J. Sambrook et al., Molecular Cloning; A Laboratory Manual, Cold Spring Harbor Laboratory press (2d ed., 1989), provides suitable methods of construction.

Aside from recombinant DNA sequence that serve as transcription units for LANA or other portions thereof, a portion of the recombinant DNA may be untranscribed, serving a regulatory or a structural function.

The recombinant DNA sequence to be introduced into the cells further will generally contain either a selectable marker gene or a reporter gene or both to facilitate identification and selection of transformed cells. Alternatively, the selectable marker may be carried on a separate piece of DNA and used in a co-transformation procedure. Both selectable markers and reporter genes may be flanked with appropriate regulatory sequences to enable expression in mammalian cells. Useful selectable markers are well known in the art and include, for example, anti-biotic and herbicide resistance genes.

Sources of DNA sequences useful in the present invention include Poly-A RNA from mammalian cells, from which the mRNA encoding LANA can be derived and used for the synthesis of the corresponding cDNA by methods known to the art. Such sources include cDNA libraries and mRNA pools made from neuronal, neuroblastoma, embryonic, fetal, and hematopoietic tissues of human, rat or other mammalian origin.

Selectable marker genes encoding enzymes which impart resistance to biocidal compounds are listed in Table 1, below.

TABLE 3

Selectable Marker Genes

| Resistance Gene or Enzyme | Confers Resistance to: | Reference |
|---|---|---|
| Neomycin phosphotransferase (neo) | G-418, neomycin, kanamycin | Southern et al., 1982, J. Mol. Appl. Gen., 1:327–341 |
| Hygromycin phosphotransferase (hpt or hyg) | Hygromycin B | Shimizu et al., 1986, Mol. Cell Biol., 6:1074–1087 |

TABLE 3-continued

Selectable Marker Genes

| Resistance Gene or Enzyme | Confers Resistance to: | Reference |
|---|---|---|
| Dihydrofolate reductase (dhfr) | Methotrexate | Kwok et al., 1986, Proc. Nat'l. Acad. Sci. USA, 4552–4555 |
| Phosphinothricin acetyltransferase (bar) | Phosphinothricin | DeBlock et al., 1987, EMBO J., 6:2513–2518 |
| 2,2-Dichloropropionic acid dehalogenase | 2-2,Dichloropropionic acid (Dalapon) | Buchanan-Wollaston et al., 1989, J. Cell. Biochem., Supp. 13D, 330 |
| Acetohydroxyacid synthase | Sulfonylurea, imidazolinone and triazolopyrimidine herbicides | Anderson et al. (U.S. Pat. No. 4,761,373); G. W. Haughn et al., 1988 Mol. Gen. Genet., 211:266–271 |
| 5-Enol-pyruvylshikimate phos-phate synthase (aroA) | Glyphosate | Comai et al., 1985 Nature, 317:741–744 |
| Haloarylnitrilase | Bromoxynil | Stalker et al., published PCT appln. W087/04181 |
| Acetyl-coenzyme A carboxylase | Sethoxydim, haloxyfop | Parker et al., 1990 Plant Physiol., 92:1220 |
| Dihydropteroate synthase (sul I) | Sulfonamide herbicides | Guerineau et al., 1990, Plant Molec. Biol., 15:127–136 |
| 32 kD photosystem II polypeptide (psbA) | Triazine herbicides | Hirschberg et al., 1983, Science, 222:1346–1349 |
| Anthranilate synthase | 5-Methyltryptophan | Hibberd et al. (U.S. Pat. No. 4,581,847) |
| Dihydrodipicolinic acid synthase (dap A) | Aminoethyl cysteine | Glassman et al., published PCT application No. W089/11789 |

Reporter genes are used for identifying potentially transformed cells and for evaluating the functionality of regulatory sequences. Reporter genes which encode for easily assayable marker proteins are well known in the art. In general, a reporter gene is a gene which is not present in or expressed by the recipient organism or tissue and which encodes a protein whose expression is manifested by some easily detectable property, e.g., enzymatic activity. Preferred genes includes the chloramphenicol acetyl transferase gene (cat) from Tn9 of E. coli, the betagalactosidase gene of E. coli, the beta-glucuronidase gene (gus) of the uida locus of E. coli, and the luciferase gene from firefly Photinus pyralis. Expression of the reporter gene is assayed at a suitable time after the DNA has been introduced into the recipient cells.

Other elements such as introns, enhancers, polyadenylation sequences and the like, may also be a part of the recombinant DNA sequence. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

5.2. Biology of the RVCAE

The RVCAE's of the present invention include any RVCAE from any rhodino virus. According to one embodiment of the invention the RVCAE element includes at least one copy of the rhodino virus terminal repeat (TR). According to another embodiment of the invention, the RVCAE element includes at least three copies of the rhodino virus terminal repeat (TR) and 0.6 kb of the rhodino virus adjacent unique DNA.

A large isolated RVCAE from KSHV is the entire Z6 element. The smallest RVCAE demonstrated as being able to permit stable episome persistence in LANA expressing cells is described in the examples, infra, as the KSHV TR as reported in Russo et al., PNAS, 93, 14862–14867 (1996), and as set forth in FIG. 8, supra, SEQ ID NO: 3.

LANA likely binds to sequences within TR. Regions between nucleotides ~165–205, ~240–280, and ~605–650 have inverted repeats and could be origins of DNA replication within mammalian cells or LANA binding sites. Both EBV and HVS have dyad symmetry elements within their cis-acting plasmid maintenance sequences (J. Yates, N. Warren, D. Reisman, B. Sugden, Proc. *Natl. Acad. Sci. USA*, 81, 3806 (1984); J. L. Yates, N. Warren, B. Sugden, *Nature*, 313, 812 (1985); D. R. Rawlins, G. Milman, S. D. Hayward, G. S. Hayward, *Cell*, 42, 859 (1985); A. Bochkarev, et al., *Cell*, 84, 791 (1996)). "Melting" of the DNA strands could occur at A and or T rich areas. Each of these domains and flanking region sequence may be important for LANA binding and function. In addition, it is possible that any combination of these domains or other TR sequences are critical for LANA function.

5.3. Assays for Chemicals That Modulate LANA Mediated Persistence of Heterologous DNA Having RVCAE The present invention provides a simple in vitro system for the screening of drug actions on the LANA-mediated persistence of an heterologous DNA having RVCAE, which will be useful for the development of drugs and reagents that modulate LANA-mediated persistence of such DNA. Assays can be performed on living mammalian cells, which more closely approximate the effects of a particular serum level of drug in the body.

In accordance with the methods and assays of the present invention, a plasmid (GFP-RVCAE) may be generated to express the green fluorescent protein (GFP) (or other reporter gene) and the neomycin resistance gene (or other selection gene) from constitutive promoters (such as the SV40 and TK promoters) and which also contains the RVCAE. GFP-RVCAE may be transfected into BJAB/LANA or BJAB/F-LANA cells or into LANA negative BJAB cells and selected for G418 resistance conferred by the neomycin resistance gene as described in the examples at Section 8, infra. The G418 resistant cells are assayed by Gardella gel analysis (Gardella, T., et al., *Journal of Virology*, 50, 248–254 (1984)) for the presence of the episomal DNA. G418 resistant, GFP-RVCAE transfected, BJAB/LANA or BJAB/F-LANA cells will have episomal DNA but G418 resistant, GFP-RVCAE transfected, LANA negative BJAB cells will not have episomal DNA. The G418 resistant cells may then be assayed by immunofluorescent microscopy for GFP expression.

Cells that are useful in practicing the screening assays of the present invention include GFP expressing, G418 resistant, GFP-RVCAE transfected, BJAB/LANA or BJAB/F-LANA cells that have episomal DNA (GFP/BJAB/LANA or GFP/BJAB/F-LANA, respectively) and GFP expressing, G418 resistant, GFP-RVCAE transfected, BJAB cells that do not have episomal DNA (GFP/BJAB). GFP/BJAB/LANA or GFP/BJAB/F-LANA cells and GFP/BJAB cells which express similar levels of GFP may be plated at low concentration into microwell plates in G418 containing medium and incubated at 37° C. to allow for cell growth (Harada, et al., *J. Virology*, 72, 9948–58 (1998)).

In accordance with the assays of the present invention, chemicals to be assayed for the ability to modulate the LANA-mediated persistence of an heterologous DNA having RVCAE may also be added to the medium. Chemicals that interrupt LANA mediated episome persistence, for example, may be identified by their ability to prevent growth of GFP/BJAB/LANA or GFP/BJAB/F-LANA cells since the neomycin resistance gene is expected to be primarily episomal and is necessary to prevent cell death in the presence of G418. In contrast, GFP/BJAB cells have GFP-RVCAE integrated into chromosomes and will continue to proliferate in the presence of an otherwise non-toxic chemical. After allowing for cell growth to occur, a plate reader may assay for GFP expression in each well. A chemical that interferes the LANA-mediated persistence of an heterologous DNA having RVCAE may be identified by its ability to greatly diminish GFP expression in the GFP/BJAB/LANA or GFP/BJAB/F-LANA wells compared to the GFP/BJAB wells. A chemical that enhances the LANA-mediated persistence of a plasmid DNA as an episome or increases its copy number can be identified by its ability to increase GFP expression.

5.4. Assays for Chemicals That Interfere With LANA'S Interaction With KSHV DNA In order to screen for chemicals which interfere with F-LANA's binding to the KSHV cis-acting element, F-LANA may be affinity purified from BJAB/F-LANA stable cell lines using the N-terminal FLAG epitope. BJAB/F-LANA cells will be lysed in 1% NP40 buffer (such as 50 mM Tris pH 7.5, 150 mM NaCl, 1% P40, 10 $\mu$g/ml leupeptin, 1 mM PMSF and 10 $\mu$g/ml aprotinin) and F-LANA loaded on an M2 anti-FLAG monoclonal antibody affinity gel column (Sigma) with multiple passes of the extract. After three washes with TBS, F-LANA may be eluted off the column by competition with FLAG peptide (Sigma). Centricon centrifuge tubes with an appropriate MW cutoff may then be used to purify the F-LANA from the FLAG peptide. F-LANA will be quantitated by BCA Protein Assay Reagent (Pierce) and assayed for purity by SDS-PAGE and Coomassie staining. Initially $5\times10^7$ BJAB/F-LANA cells will be used. Depending on the yield of F-LANA, the number of cells can be scaled up accordingly in order to obtain enough protein for the assays outlined below. It is well within the skill of one in the art to perform this purification using commercially available reagents and other technologies such as those from Sigma.

Alternatively, bacterially expressed LANA may also be assayed for DNA binding to the KSHV cis-acting element. If binding activity is retained with bacterially expressed LANA, then the bacterially expressed LANA or F-LANA may be used for assays. LANA may be fused in frame with glutathione S-transferase (GST) in pGEX-2TK (Kaelin, W. G., et al., *Cell*, 70, 351–64 (1992)). GST-LANA may be expressed in *E. coli* and purified with glutathione beads. Quantitation of the GST fusion proteins and assay of purity may be performed as above. A thrombin cleavage site may be used to cleave glutathione S-transferase from the rest of the fusion protein. The purified F-LANA or bacterially expressed LANA may be biotin labeled.

The KSHV RVCAE may be purified (e.g., released by restriction endonuclease from a plasmid clone and electrophoresed on an agarose gel) and bound to a matrix such as agarose beads. Protein binding to the TR matrix with biotin labeled, purified F-LANA or bacterially expressed LANA may be carried out in an appropriate binding buffer which includes excess nonspecific DNA such as salmon sperm DNA. Chemicals to be assayed may also be added to the incubation. After an appropriate incubation time, the RVCAE matrix may be washed with an appropriate wash buffer. In order to detect biotin labeled F-LANA or bacterially expressed LANA bound to the TR matix, binding with streptavidin-HRP (or another appropriate conjugate) may be performed, followed by appropriate washes and then incubation with a calorimetric substrate. An ELISA plate reader may be used to quantitate the amount of bound F-LANA or bacterially expressed LANA as determined by the amount of colored product produced. Chemicals which interfere with LANA binding to the KSHV RVCAE cis-acting element may be identified by a resulting reduction in the amount of colored product produced. Chemicals that enhance LANA binding to RVCAE may be identified by a resulting increase in the amount of colored product produced.

5.5. Gene Therapies

A variety of gene therapy approaches may be used in accordance with the invention. For example, antisense DNA molecules may be engineered and used to block translation of mRNA in vivo. Alternatively, ribozyme molecules may be designed to cleave and destroy the mRNAs in vivo. In another alternative, oligonucleotides designed to hybridize to the 5' region of a gene (including the region upstream of the coding sequence) and form triple helix structures may be used to block or reduce transcription of the gene. In yet another alternative, nucleic acid encoding the full length wild-type message may be introduced in vivo into cells which otherwise would be unable to produce the wild-type gene produce in sufficient quantities or at all.

In a preferred embodiment, the antisense, ribozyme and triple helix nucleotides are designed to inhibit the translation or transcription of a gene. To accomplish this, the oligonucleotides used should be designed on the basis of relevant sequences unique to that gene. For example, and not by way of limitation, the oligonucleotides should not fall within those regions where the nucleotide sequence of the gene is most homologous to that of other known proteins.

Instead, it is preferred that the oligonucleotides fall within the regions of the gene, which diverge from the sequence of other known proteins.

In the case of antisense molecules, it is preferred that the sequence be chosen from those divergent sequences just mentioned above. It is also preferred that the sequence be at least 18 nucleotides in length in order to achieve sufficiently strong annealing to the target mRNA sequence to prevent translation of the sequence. Izant and Weintraub, 1984, Cell, 36: 1007–1015; Rosenberg et al., 1985, Nature, 313: 703–706.

In the case of the "hammerhead" type of ribozymes, it is also preferred that the target sequences of the ribozymes be chosen from the above-mentioned divergent sequences. Ribozymes are RNA molecules which possess highly specific endoribonuclease activity. Hammerhead ribozymes comprise a hybridizing region which is complementary in nucleotide sequence to at least part of the target RNA, and a catalytic region which is adapted to cleave the target RNA. The hybridizing region contains nine (9) or more nucleotides. Therefore, the hammerhead ribozymes of the present invention have a hybridizing region which is complementary to the sequences listed above and is at least nine nucleotides in length. The construction and production of such ribozymes is well known in the art and is described more fully in Haseloff and Gerlach, 1988, Nature, 334: 585–591.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574–578; Zaug and Cech, 1986, Science, 231: 470–475; Zaug, et al., 1986, Nature, 324:429–433; published International patent application No. WO88/04300 by University Patents, Inc.; Been and Cech, 1986, Cell, 47: 207–216). The Cech endoribonucleases have an eight base pair active site which hybridizes to a target RNA sequence whereafter cleavage of the target RNA takes place.

In the case of oligonucleotides that hybridize to and form triple helix structures at the 5' terminus of the gene and can be used to bock transcription, it is preferred that they be complementary to those sequences in the 5' terminus of the gene which are not present in other related proteins. However, it is preferred that the sequences not include those regions of the gene's promoter which are even slightly homologous to that of other known proteins.

The foregoing compounds can be administered by a variety of methods which are known in the art including, but not limited to the use of liposomes as a delivery vehicle. Naked DNA or RNA molecules may also be used where they are in a form which is resistant to degradation such as by modification of the ends, by the formation of circular molecules, or by the use of alternate bonds including phosphothionate and thiophosphoryl modified bonds. In addition, the delivery of nucleic acid may be by facilitated transport where the nucleic acid molecules are conjugated to poly-lysine or transferrin. Nucleic acid may also be transported into cells by any of the various viral carriers, including but not limited to, retrovirus, vaccinia, AAV, and adenovirus.

Alternatively, a recombinant nucleic acid molecule which encodes, or is, such antisense, ribozyme, or triple helix, can be constructed. This nucleic acid molecule may be either RNA or DNA. If the nucleic acid encodes an RNA, it is preferred that the sequence be operatively attached to a regulatory element so that sufficient copies of the desired RNA product are produced. The regulatory element may permit either constitutive or regulated transcription of the sequence. In vivo, that is, within the cells or cells of an organism, a transfer vector such as a bacterial plasmid or viral RNA or DNA, encoding one or more of the RNAs, may be transfected into cells e.g. (Llewellyn et al., 1987, J. Mol. Biol., 195: 115–123; Hanahan et al. 1983, J. Mol. Biol., 166: 557–580). Once inside the cell, the transfer vector may replicate, and be transcribed by cellular polymerases to produce the RNA or it may be integrated into the genome of the host cell. Alternatively, a transfer vector containing sequences encoding one or more of the RNAs may be transfected into cells or introduced into cells by way of micromanipulation techniques such as microinjection, such that the transfer vector or a part thereof becomes integrated into the genome of the host cell.

6. EXAMPLE

LANA is Restricted to Sites of KSHV DNA

The previously described punctate distribution (P. Kellam, et al., *J. of Human Virol.*, 1, 19 (1997); L. Rainbow, et al., *J. Virol.*, 71, 5915 (1997); D. H. Kedes, M. Lagunoff, R. Renne, D. Ganem, *J. Clin. Invest.*, 100, 2606 (1997); F. Neipel, J. C. Albrecht, B. Fleckenstein, *J. Virol.*, 71, 4187 (1997); S. J. Gao, et al., *Nature Medicine*, 2, 925 (1996); D. H. Kedes, et al., *Nature Medicine*, 2, 918 (1996); D. Jones, et al., *N. Engl. J. of Med.*, 339, 444 (1998); R. Renne, et al., *Nature Medicine*, 2, 342 (1996); L. Szekely, et al., *J. of General Virology*, 79, 1445 (1998)) of LANA in PEL cells was -further investigated by confocal microscopy. LANA was detected with immune serum and KSHV DNA was detected by fluorescent in situ hybridization (FISH) in KSHV infected BCBL-1 PEL cells (S. J. Gao, et al., *Nature Medicine*, 2, 925 (1996); D. H. Kedes, et al., *Nature Medicine*, 2, 918 (1996); D. Jones, et al., *N. Engl. J. of Med.*, 339, 444 (1998); R. Renne, et al., *Nature Medicine*, 2, 342 (1996); see also the examples at Section 10, infra). Two color confocal microscopy demonstrated that LANA (FIG. 1A, green signal) and KSHV DNA (FIG. 1B, red signal) colocalized (FIG. 1C, yellow signal) in subnuclear dots that were multiple, small, and discrete. Each dot probably corresponds to a KSHV DNA episome since approximately 40 dots were visualized per nucleus, which is consistent with estimates of the KSHV genome copy number per cell (E. Cesarman, et al., *Blood*, 86, 2708 (1995); M. B. Rettig, et al., *Science*, 276, 1851 (1997); J. Soulier, et al., *Blood*, 86, 1276 (1995)); E. Cesarman, Y. Chang, P. S. Moore, J. W. Said, D. M. Knowles, *N. Engl. J. Med.*, 332, 1186 (1995)). LANA was highly concentrated at sites of KSHV DNA. The finding that LANA is restricted to sites of KSHV DNA in interphase was previously unknown and is indicative of specific recognition of KSHV DNA by LANA.

7. EXAMPLE

LANA Colocalizes With KSHV DNA and Chromosomes During Mitosis

Figure 2:
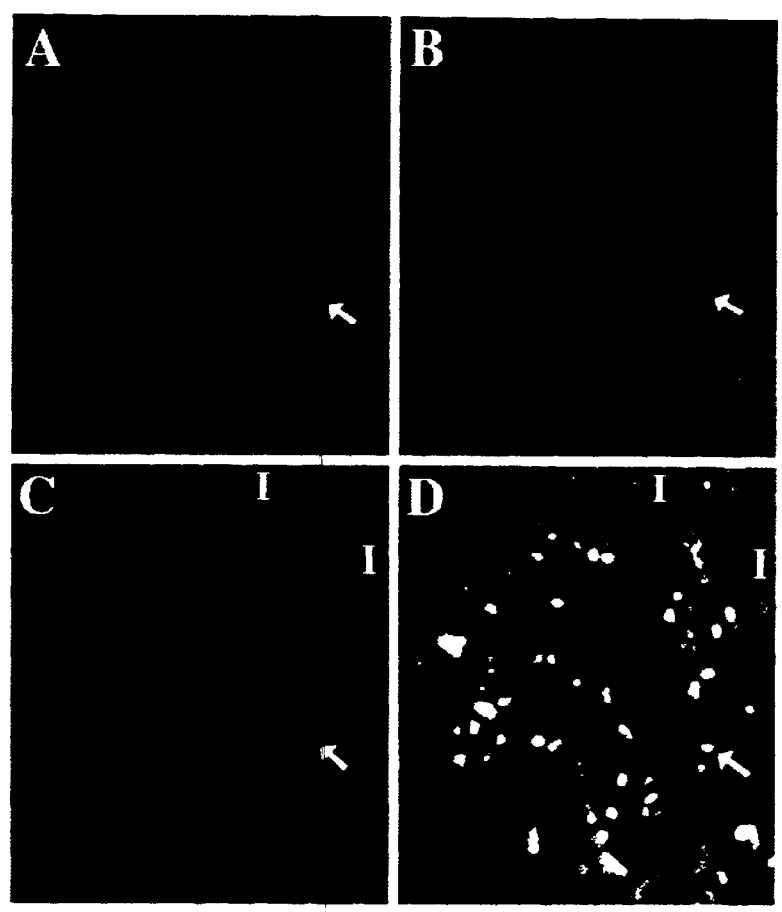

We next investigated whether the association of LANA and KSHV DNA persisted in mitosis. LANA (L. Szekely, et al., *J. of General Virology*, 79, 1445 (1998)) and KSHV DNA (E. Cesarman, et al., *Blood*, 86, 2708 (1995)) associate with mitotic chromosomes in PEL cells. Colocalization of LANA and KSHV DNA on chromosomes would be consistent with a role for LANA in episome persistence. We detected KSHV DNA in BCBL-1 cells by FISH (FIG. 2A, red signal), and we detected LANA by immune serum (FIG. 2B, green signal). We detected chromosomes with 4',6'-diamidino-2-phenylindole (DAPI) (FIG. 2C, blue signal). (See Examples at Section 10, infra) An overlay of the same chromosome spread (as shown in FIG. 2A, B, and C) revealed LANA to be highly localized to sites of KSHV DNA and both LANA and KSHV DNA were in dots dispersed widely over the metaphase chromosomes without apparent regularity (FIG. 2D, punctate white on blue chromosomes). The finding that LANA colocalizes with KSHV genomes on metaphase chromosomes is consistent with a model in which LANA mediates the segregation of KSHV episomes to progeny cells by linking KSHV DNA to chromosomes during mitosis.

Although LANA and EBNA1 share the property of diffuse association with chromosomes in the absence of cognate viral DNA, LANA differs from EBNA1 in highly localizing to its cognate DNA. KSHV DNA can recruit a significant fraction of the LANA molecules in the cell. In contrast, EBNA1 is diffusely distributed on metaphase chromosomes even in the presence of EBV DNA (D. R. Rawlins, G. Milman, S. D. Hayward, G. S. Hayward, *Cell*, 42, 859 (1985); L. Petti, C. Sample, E. Kieff, *Virology*,. 176, 563 (1990); E. Grogan, et al., *Proc. Natl. Acad. Sci. USA*, 80, 7650 (1983); B. M. Reedman, G. Klein, *Int. J. Cancer*, 11, 499 (1973)). LANA and EBNA1 also lack obvious sequence homology. However, EBNA1 shares structural and functional characteristics with the nonhomologous bovine papillomavirus (BPV) E2 protein (A. Bochkarev, et al., *Cell*, 84, 791 (1996)) and LANA could have similar structural features.

8. EXAMPLE

LANA Acts in Trans on a Cis-acting Element in Z6 to Efficiently Mediate Z6 Episome Persistance in Cells If this model were correct, LANA, independent of other KSHV proteins, should mediate KSHV episome persistence in proliferating cells. To directly test this hypothesis, we stably expressed LANA or a FLAG-tagged LANA (F-LANA) in KSHV and EBV negative BJAB B lymphoma cells. (See Examples at Section 10, infra) Because the HVS oriP is located near the start of the viral genome (S. -H. Kung, P. G. Medveczky, *J. Virol.*, 70, 1738 (1996)), and because the KSHV genome is generally colinear with that of HVS, we considered the possibility that the KSHV orip is in a cosmid clone (Z6) (J. J. Russo, et al., *Proc. Natl. Acad. Sci. USA*, 93, 14862 (1996)) that contains the terminal repeats and start of the KSHV genome. Z6 or Z8 (J. J. Russo, et al., *Proc. Natl. Acad. Sci. USA*, 93, 14862 (1996)) cosmid that contains sequence from near the center of the KSHV genome, were transfected into BJAB cells or into LANA- or F-LANA-expressing BJAB cells (BJAB/LANA or BJAB/F-LANA, respectively). Cells were selected for G418 resistance conferred by the cosmid vector. (See Examples at Section 10, infra) Z6 cosmid DNA efficiently persisted in BJAB/LANA and BJAB/F-LANA cells and almost all (99%) microtiter wells were positive for G418 resistant cell outgrowth. Efficient persistence of Z6 DNA was dependent on LANA because only 7% of wells of LANA negative BJAB cells transfected with Z6 were positive for outgrowth. In contrast to Z6, Z8 lacked a cis-acting component necessary for efficient LANA mediated outgrowth and only 3% of wells containing Z8 transfected BJAB/F-LANA cells were positive for G418 resistant outgrowth. The same low level of persistence was observed in Z8 transfected BJAB cells that were LANA negative. These results are reminiscent of those obtained with EBV oriP and EBNA1 in which EBNA1 enabled a 10–100 fold higher rate of outgrowth for cells transfected with oriP DNA compared with non-oriP DNA (J. Yates, N. Warren, D. Reisman, B. Sugden, *Proc. Natl. Acad. Sci. USA*, 81, 3806 (1984); J. L. Yates, N. Warren, B. Sugden, *Nature*, 313, 812 (1985)).

Figure 3:
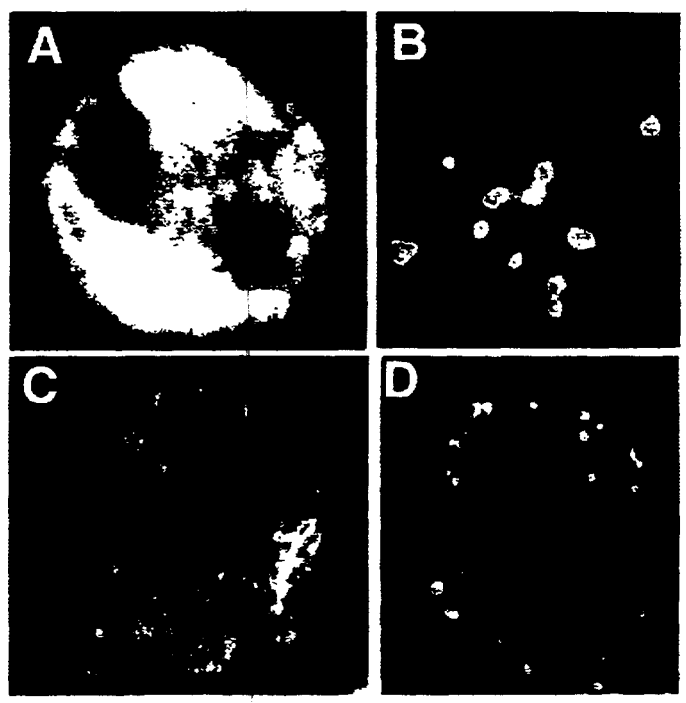

The distribution of F-LANA in BJAB cells and in the Z6 or Z8 transfected BJAB cells was investigated with immunofluorescent microsopy after detection with immune serum or monoclonal antibody to FLAG. F-LANA was distributed diffusely in interphase nuclei (FIG. 3A) and on chromosomes (FIG. 3C) in BJAB/F-LANA cells but F-LANA was focally concentrated to dots both in interphase nuclei (FIG. 3B) and along chromosomes (FIG. 3D) in BJAB/F-LANA cells that were Z6 transfected and G418 resistant. Simultaneous detection of F-LANA and Z6 DNA demonstrated that F-LANA concentrated to dots at sites of Z6 DNA. In contrast to Z6 transfected cells, F-LANA remained diffusely distributed in the nuclei of Z8 transfected, G418 resistant, BJAB/F-LANA cells. These data demonstrate that LANA specifically localizes to sites of Z6 KSHV DNA, consistent with the hypothesis that LANA serves to tether Z6 DNA to chromosomes.

If LANA mediates the efficient segregation of KSHV episomes to progeny cells, then LANA expressing cells that are Z6 transfected and G418 resistant should contain extrachromosomal Z6 DNA. Extrachromosomal DNA should rarely or never be found in G418-resistant cells that are Z6 transfected and LANA negative or Z8 transfected and LANA positive. Gardella gel analysis followed by Southern (DNA) blotting was performed to assay whether Z6 DNA is an episome in BJAB/LANA and BJAB/F-LANA cells. In Gardella gels, live cells are lysed in situ in the gel loading wells at the start of the gel run. Episomal DNA (as large as 200 kb) migrates into the gel while chromosomal DNA is unable to migrate into the gel (Gardella gels were prepared as described in T. Gardella, P. Medveczky, T. Sairenji, C. Mulder, *J. of Virol.*, 50, 248 (1984)). As expected, BCBL-1 (FIG. 4A, lane 1; FIG. 4B, lane 4) and KSHV infected BC-1 PEL cells (E. Cesarman, et al., *Blood*, 86, 2708 (1995)) (FIG. 4B, lane 2) had episomal KSHV DNA, whereas KSHV negative Raji (FIG. 4A, lane 2; FIG. 4B, lane 1) and BJAB (FIG. 4B, lane 3) cells lacked KSHV episomes. BJAB/LANA cells (FIG. 4A, lanes 3–7) or BJAB/F-LANA cells (FIG. 4A, lanes 8–12) that had grown out after transfection with Z6 DNA and G418 selection also had extrachromosomal DNA. In contrast, BJAB/F-LANA cells that had grown out after transfection with Z8 DNA and G418 selection did not have extrachromosomal ZS DNA (FIG. 4B, lanes 5–12). Also, LANA negative BJAB cells that had grown out as G418 resistant after transfection with Z6 or Z8 did not have episomal DNA. These latter cells had Z6 or Z8 DNA by polymerase chain reaction (PCR), and Z6 or Z8 DNA was sometimes detected at the loading wells on long exposures of Southern blots of Gardella gels, which is consistent with the presence of integrated DNA in these cells. These experiments demonstrate that LANA acts in trans on a cis-acting element present in Z6 to efficiently mediate Z6 episome persistence in cells.

9. EXAMPLE

LANA Acts in Trans on a 0.8 Kb KSHV TR Unit to Mediate Efficient Episome Persistence To more precisely localize the Z6 cis-acting element, Hind III subclones of Z6 cosmid DNA were transfected into BJAB or BJAB/F-LANA cells and selected for G418 resistance (See Example 14, infra) A Z6 subclone containing the terminal repeats, 0.6 kb of unique DNA, and the first ~13 kb of the KSHV genome (Z6-13) efficiently persisted as an episome in G418 resistant BJAB/F-LANA cells (FIG. 4C, lanes 6–9). In contrast, the fewer BJAB/F-LANA cells that had grown out as G418 resistant after transfection of Hind III subclones containing ~7 or ~11 kb of downstream KSHV sequence (Z6-7 and Z6-11, respectively) did not have extrachromosomal Z6-7 (FIG. 4C, lanes 12, 13) or Z6-11 DNA. LANA-negative BJAB cells that had grown out as G418 resistant after transfection with Z6-13 (FIG. 4C, lanes 4, 5), Z6-7 (FIG. 4C, lanes 10, 11) or Z6-11 DNA did not have episomal DNA. Therefore, LANA acts in trans on a cis-acting element in the terminal repeats, the 0.6 kb of unique DNA, or the first ~13 kb of unique KSHV DNA from Z6 to mediate efficient episome persistence.

Having showed that LANA acts in trans on a KSHV cis-acting element present in a region of Z6 DNA which contains the terminal repeats (TR), the ~0.6 kb of unique sequence, and the first ~13 kb of the KSHV genome (the Z6-13 construct), additional experiments were condcuted to determine whether the cis-acting element can be localized to a smaller unit within the KSHV TR.

Subclones of the Z6 cosmid were constructed. To generate the Z6-U8TRU construct, an EcoR1/Bg1II fragment of the Z6-13 construct was subcloned into the XhoI/BamH1 site of a modified pRep9 vector (Invitrogen). The Z6-U8TRU construct encompasses the entire 6.5 kb TR found in the KSHV infected cell line BC-1 plus unique (U) KSHV DNA sequence. The unique sequence in Z6-U8TRU includes the first ~1.3 kb of the genome and also ~0.6 kb of additional sequence. Further subcloning from the Z6-U8TRU construct was done to delineate a minimal cis-acting element that could be maintained as an episome when LANA is provided in trans. To generate clones Z6-3TRU and Z6-1TR, the Z6-13 construct was digested with NotI and the 0.8 kb TR and 0.6 kb unique DNA fragment were purified and ligated into the NotI site of a modified pRep9 vector which was previously deleted for sequence between ClaI and KpnI. Z6-3TRU contains 3 copies of the 0.8 kb NotI TR fragment and 1 copy of the 0.6 kb, unique NotI DNA fragment. Z6-1TR contains one copy of the 0.8 kb NotI terminal repeat fragment. The modified pRep9 vectors encode the neomycin resistance gene downstream of a TK promoter which provides G418 resistance.

Figure 5:
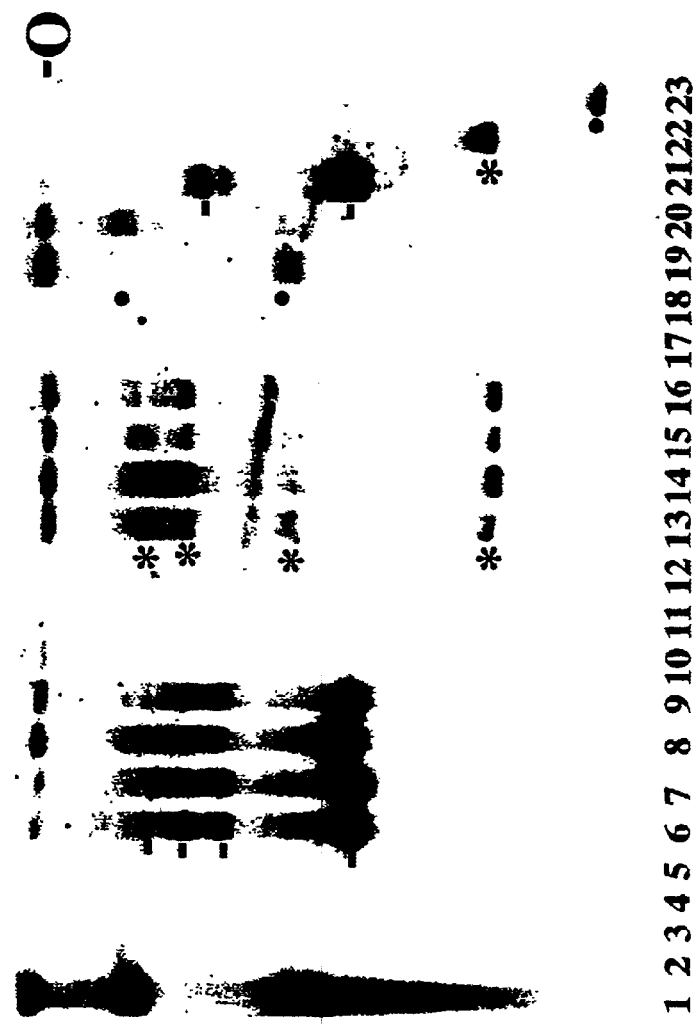

To determine the minimal sequence of Z6 that is required for episomal maintenance in LANA expressing cells, subclones of the Z6 cosmid in pRep9 were transfected into BJAB or BJAB/F-LANA cells and G418 resistant lines were selected over an ~2 week period. A high frequency of positive selection was observed in F-LANA/BJAB cells transfected with Z6-U8TRU, Z6-3TRU, or Z6-1TR (100% of wells for all three clones) whereas only ~16, 45, and 16% of wells with LANA negative BJAB cells transfected with Z6-U8TRU, Z6-3TRU, or Z6-1TR, respectively, were positive for G418-resistant outgrowth. KSHV DNA presence in the cell lines was assayed by Gardella cell gels. Z6 subclones Z6-U8TRU (FIG. 5, lanes 6–9), which contains the terminal repeats, the first ~1.3 kb of the KSHV genome and an additional ~0.6 kb of unique sequence, and Z6-3TRU (FIG. 5, lanes 13–16) efficiently persisted as episomes in G418-resistant BJAB/F-LANA cells. Z6-1TR transfected F-LANA/BJAB cells also had extrachromosomal DNA (FIG. 5, lanes 19 and 20). As expected, LANA negative BJAB cells that had grown out after transfection with Z6-U8TRU, Z6-3TRU, or Z6-1TR did not have extrachromosomal DNA (FIG. 5 lanes 3–5, lanes 10–12, and lanes 17 and 18, respectively). KSHV infected BCBL-1 cells (FIG. 5, lane 1) had KSHV episomes whereas the KSHV negative cell line BJAB (FIG. 5, lane 2) did not. These data demonstrate that LANA acts in trans on a cis-acting element that is within the single copy TR DNA to mediate efficient episome persistence.

10. EXAMPLE

Additional Materials and Methods

Fluorescent in situ hybridization (FISH) was performed with TSA™-Direct (NEN Life Science Products). Colcemid treatment and hypotonic swelling of cells was performed as described in D. Reisman, B. Sugden, *Molecular and Cellular Biology*, 6, 3838 (1986). Cells were fixed in 4% paraformaldehyde at room temperature for 10 min followed by 70% ethanol at 4° C. for 10 min. Fixed cells were permeabilized with 0.5% Triton-X 100, and overlayed with DNA in situ hybridization solution (DAKO) containing 20 ng of a biotin-labeled, nick translated, probe from pBSLANA. pBSLANA was constructed by subcloning the 4.7 kb KSHV genomic SacI fragment flanking ORF73 from the L54 library phage (J. J. Russo, et al., *Proc. Natl. Acad. Sci. USA*, 93, 14862 (1996)) into pBluescript (Stratagene). After denaturation of DNA at 93° C. for 5 min, slides were incubated for 4 h at 370° C., washed in 0.2×SSC for 30 min at 45° C., and blocked in TNB (0.1 M Tris-HCl, pH 7.5, 0.15 M NaCl, 0.5% blocking reagent) at room temperature for 30 min. Slides were then incubated with streptavidin-HRP (1:100) for 30 min at 37° C., followed by incubation with cyanine 3-tyramide (1:50) for 10 min at room temperature. After FISH, cells were incubated with BJAB cell extract adsorbed KSHV-immune serum (1:50) followed by secondary FITC-conjugated antibody and counterstained with 4',6-diamidine-2'-phenylindole dihydrochloride (DAPI, 1 μg/ml) in methanol for 15 min. For two color fluorescence, DAPI was omitted.

Genomic ORF73 was cloned downstream of the SV40 promoter in pSG5 (Stratagene) (termed pSG5LANA) or in pSG5FLAG (E. Hatzivassiliou, P. Cardot, V. I. Zannis, S. A. Mitsialis, *Biochemistry*, 36, 9221 (1997)) (termed pSG5 F-LANA). In pSG5 F-LANA, the four N-terminal LANA amino acids are replaced with the FLAG epitope (DYKDDDDKV). LANA stable cell lines were generated by electroporating pSG5LANA or pSG5 F-LANA and a plasmid encoding the hygromycin resistance gene downstream of an SV40 promoter into BJAB cells (K. M. Kaye, K. M. Izumi, G. Mosialos, E. Kieff, *J. of Virol.*, 69, 675 (1995); D. Liebowitz, J. Mannick, K. Takada, E. Kieff, *J. of Virol.*, 66, 4612 (1992)). After 48 h, cells were seeded into microtiter plates and hygromycin resistant clones selected. Hygromycin resistant BJAB cells expressing pSG5LANA (BJAB/LANA) or pSG5 F-LANA (BJAB/F-LANA) were transfected with 25 μg of the Z6 or Z8 cosmid. Z6 contains KSHV sequence including the terminal 5 repeats and the first -33 kb of the BC-1 genome cloned into S-Cos1 (Stratagene) and Z8 contains nucleotides ~73,000–107,000 of BC-1 KSHV cloned into S-Cos1 (J. J. Russo, et al., *Proc. Natl. Acad. Sci. USA*, 93, 14862 (1996)). S-Cos1 encodes the neomycin resistance gene downstream of an SV40 promoter and provides G418 resistance. After 48 h, cells were placed under G418 selection. For subclone analysis, the Z6 cosmid was digested with HindIII and religated resulting in deletion of KSHV sequences after the first ~13 kb of the genome (Z6-13). The two largest remaining Z6 KSHV HindIII fragments of ~7 and ~11 kb were cloned into pREP9 (Invitrogen) after deletion of the pREP9 sequences between ClaI and KpnI (Z6-7 and Z6-11 respectively). pREP9 encodes the neomycin resistance gene downstream of a TK promoter and provides G418 resistance. The Z6 subclones were transfected into BJAB/F-LANA or BJAB cells and selected for G418 resistance as above.

The present invention is not limited in scope by the specific embodiments described herein. Modifications thereof will become apparent to those in the art based on the teachings of the forgoing description and drawings. Such modifications fall within the scope of the claimed invention.

What is claimed is:

1. A method for evaluating the presence or degree of a compound's ability to modulate LANA (SEQ ID NO 2) mediated persistence or expression in a cell of a DNA episome having RVCAE (SEQ ID NO 3) comprising:
   (a) Having cells containing LANA (SEQ ID NO 2) and a persisting DNA episome having RVCAE (SEQ ID NO 3) wherein the presence of the episome is assayed by measurement of episome DNA or episome based expression of a selection or reporter gene;
   (b) Adding the compound to the medium of some of the cells; and
   (c) Comparing the results of the assay from cells exposed to the compound against that from cells not exposed to the compound.

2. A method for evaluating the presence or degree of a compound's ability to modulate binding between LANA (SEQ ID NO 2) and RVCAE (SEQ ID NO 3) or between LANA (SEQ ID NO 2) and LANA (SEQ ID NO 2) comprising:
   (a) Associating with a matrix or surface a first reagent selected from the group consisting of LANA (SEQ ID NO 2) and RVCAE (SEQ ID NO 3);
   (b) Adding a solution comprising the compound; and
   (c) Adding to the solution a second reagent selected from the group consisting of LANA (SEQ ID NO 2) or RVCAE (SEQ ID NO 3); and
   (d) Evaluating the presence or degree of binding of the second reagent to the first reagent.

3. The method of claim 2, wherein the evaluation of binding is conducted using physical, chemical, biological, radiological, photometric, immunologic, or enzymatic properties inherent in or attached to one or more of the reagents or compound.

4. A kit for practicing the method of claim 1.

5. A kit for practicing the method of claim 2.

6. A kit for practicing the method of claim 3.

* * * * *